(12) United States Patent
Banks et al.

(10) Patent No.: US 9,618,450 B2
(45) Date of Patent: Apr. 11, 2017

(54) MULTI-CHANNEL FLUOROMETRIC SENSOR AND METHOD OF USING SAME

(71) Applicant: ECOLAB USA INC., St. Paul, MN (US)

(72) Inventors: Rodney H. Banks, Aurora, IL (US); Eugene Tokhtuev, Duluth, MN (US)

(73) Assignee: ECOLAB USA, INC., Saint Paul, MN (US)

( * ) Notice: Subject to any disclaimer, the term of this patent is extended or adjusted under 35 U.S.C. 154(b) by 0 days.

(21) Appl. No.: 14/039,683

(22) Filed: Sep. 27, 2013

(65) Prior Publication Data

US 2015/0090900 A1   Apr. 2, 2015

(51) Int. Cl.
| | | |
|---|---|---|
| G01N 21/00 | (2006.01) | |
| G01N 21/64 | (2006.01) | |
| G01N 21/53 | (2006.01) | |

(52) U.S. Cl.
CPC .......... *G01N 21/645* (2013.01); *G01N 21/53* (2013.01)

(58) Field of Classification Search
CPC ............................... G01N 21/00; G01N 33/00
USPC ............... 356/432, 337, 338, 336, 344, 317; 436/176
See application file for complete search history.

(56) References Cited

U.S. PATENT DOCUMENTS

| | | | |
|---|---|---|---|
| 5,894,347 A * | 4/1999 | MacDonald | ................... 356/317 |
| 6,089,242 A | 7/2000 | Buck | |
| 6,369,894 B1 | 4/2002 | Rasimas et al. | |
| 6,396,069 B1 | 5/2002 | MacPherson et al. | |
| 6,423,152 B1 | 7/2002 | Landaas | |
| 6,767,408 B2 | 7/2004 | Kenowski et al. | |
| 6,870,165 B2 * | 3/2005 | Amirkhanian et al. | ... 250/458.1 |
| 7,060,136 B1 | 6/2006 | Zeiher et al. | |
| 7,099,012 B1 | 8/2006 | Crawford et al. | |
| 7,106,442 B2 * | 9/2006 | Silcott et al. | ................. 356/338 |
| 7,247,210 B2 | 7/2007 | Staub et al. | |
| 7,416,701 B2 | 8/2008 | Tokhtuev et al. | |
| 7,491,366 B2 | 2/2009 | Tokhtuev et al. | |

(Continued)

OTHER PUBLICATIONS

U.S. Appl. No. 13/437,573, filed Apr. 2, 2012, entitled "Flow Chamber for Online Fluometer".

(Continued)

*Primary Examiner* — Tarifur Chowdhury
*Assistant Examiner* — Isiaka Akanbi
(74) *Attorney, Agent, or Firm* — Fredrikson & Byron, P.A.

(57) ABSTRACT

An optical sensor may include multiple optical emitters configured to emit light into a fluid sample via an optical pathway. Light from the emitters can cause fluorescence from the sample and/or scatter off of the sample. Scattered and fluoresced light can be received by an optical detector in the sensor via the optical pathway, and used to determine at least one characteristic of the fluid sample. A second optical detector can provide reference measurements of the amount of light emitted to the sample. In one example, the optical detector can detect scattered and fluoresced light simultaneously. In another example, light is emitted and detected alternatingly. The sensor can be part of a system that includes one or more controllers configured to control the emitting and detecting of light to and from the fluid sample. The controller can use detected light to determine at least one characteristic of the fluid sample.

58 Claims, 15 Drawing Sheets

(56) References Cited

U.S. PATENT DOCUMENTS

| | | | |
|---|---|---|---|
| 7,582,882 B2 * | 9/2009 | McLoskey | G01J 3/10 250/458.1 |
| 7,614,410 B2 | 11/2009 | Kenowski et al. | |
| 7,652,267 B2 | 1/2010 | Tokhtuev et al. | |
| 7,989,780 B2 | 8/2011 | Tokhtuev et al. | |
| 8,248,611 B2 | 8/2012 | Christensen et al. | |
| 8,269,193 B2 | 9/2012 | Christensen et al. | |
| 8,269,966 B2 * | 9/2012 | Gruler | 356/318 |
| 8,352,207 B2 | 1/2013 | Tokhtuev et al. | |
| 8,373,140 B2 | 2/2013 | Tokhtuev et al. | |
| 2005/0168741 A1 * | 8/2005 | Banks | 356/417 |
| 2006/0176479 A1 * | 8/2006 | Laurence | G01J 1/42 356/317 |
| 2006/0286676 A1 | 12/2006 | Van Camp et al. | |
| 2008/0274493 A1 * | 11/2008 | Quake | B01D 57/02 435/29 |
| 2009/0059207 A1 | 3/2009 | Nerin et al. | |
| 2010/0048730 A1 | 2/2010 | Li et al. | |
| 2010/0108873 A1 | 5/2010 | Schwertner | |
| 2011/0197920 A1 | 8/2011 | Kenowski et al. | |
| 2013/0169954 A1 | 7/2013 | Gibson et al. | |
| 2013/0229657 A1 | 9/2013 | Levy et al. | |
| 2016/0258870 A1 * | 9/2016 | Tokhtuev | G01N 21/51 |

OTHER PUBLICATIONS

U.S. Appl. No. 13/464,508, filed May 4, 2012, entitled "Self-Cleaning Optical Sensor".

U.S. Appl. No. 13/796,594, filed Mar. 12, 2013, entitled "Fluorometer With Multiple Detection Channels".

International Patent Application No. PCT/US2014/057598, International Search Report and Written Opinion issued Jan. 6, 2015, 13 pages.

* cited by examiner

MULTI-CHANNEL FLUOROMETRIC SENSOR AND METHOD OF USING SAME

TECHNICAL FIELD

This disclosure relates to optical measuring devices and, more particularly, to fluorometers for monitoring the concentration of one or more substances in a sample.

BACKGROUND

In cleaning and antimicrobial operations, commercial users (e.g., restaurants, hotels, food and beverage plants, grocery stores, etc.) rely upon the concentration of a cleaning or antimicrobial product to make the product work effectively. Failure of a cleaning or antimicrobial product to work effectively (for example due to concentration issues) can cause a commercial user to perceive the product as lower quality. End consumers may also perceive the commercial provider of such products as providing inferior services. In addition, commercial users may be investigated and/or sanctioned by government regulatory and health agencies. Accordingly, there is a need for a system that can monitor the characteristics of fluid solutions, e.g., to determine if the concentration of a product is within a specified concentration range. The same may be true for other applications, such as commercial and industrial water treatment, pest control, beverage and bottling operations, oil and gas refining and processing operations, and the like.

One method of monitoring the concentration of a product relies on monitoring the fluorescence of the product that occurs when the sample (and the product within the sample) is exposed to a predetermined wavelength of light. For example, compounds within the product or a fluorescent tracer added to the product may fluoresce when exposed to certain wavelengths of light. The concentration of the product can then be determined using a fluorometer that measures the fluorescence of the compounds and calculates the concentration of the chemical based on the measured fluorescence.

Generally, fluorometric spectroscopy requires directing light from a source of radiant light to a sample and then receiving light from the sample at a detector. In order to do so, the source and detector must be in optical communication with the sample. In existing systems, providing optical access to the sample can be a costly process requiring significant modification to the system and significant downtime to perform such modification.

SUMMARY

In general, this disclosure is related to fluorometers and techniques for monitoring fluid samples. In some examples, a fluorometer according to the disclosure includes a first optical emitter configured to generate fluorescent emissions in a fluid sample under analysis and a second optical emitter configured to emit light to measure an amount of scattering in the fluid sample under analysis. The fluorometer may also include at least one detector that receives fluorescent light emitted from the fluid sample and/or light scattered from the fluid sample. During operation, the detector can detect an amount of fluorescent light emitted from the fluid sample under analysis and the fluorometer can then determine, based on the fluorescent light, a concentration of a fluorescing species in the fluid sample. The fluorometer can also detect an amount of light scattered by the fluid sample under analysis and determine, based on the scattered light, other properties of the fluid sample under analysis. For example, the fluorometer may determine a concentration of a non-fluorescing species in the fluid sample under analysis. As another example, the fluorometer may adjust the amount of fluorescent light detected based on the light scattering information, e.g., to account for the effect of fluid turbidity on the measured intensity of the fluorescent emissions.

To help provide a compact fluorometer design that is easy to install and that resists fouling, the fluorometer may be configured with a single optical lens through which light is emitted into and received from the fluid sample under analysis. The fluorometer may include a housing that contains the first optical emitter, the second optical emitter, and at least one detector. The first optical emitter, the second optical emitter, and the at least one detector may be arranged within the housing so that all the components are in optical communication with the single optical lens (e.g., can direct light through and/or receive light from the optical lens). By configuring the fluorometer with a single optical lens, the optical emitters may direct light into and the detector may receive light from substantially the same portion of fluid adjacent the optical lens. This may help avoid inconsistent optical readings that may otherwise occur if different optical emitters were to emit light through different portions of fluid through physically separate optical lenses. In addition, configuring the fluorometer with a single optical lens may provide a comparatively compact fluorometer design that can be utilized in a number of different applications. For instance, depending on the design, the fluorometer housing may be configured to be inserted into a port of a fluid vessel, a leg of a T-section of pipe, or other mechanical fitting of a process system. This can allow that fluorometer to be readily installed as an on-line fluorometer to optically monitor the process.

While the fluorometer design can vary, in some additional examples, the fluorometer includes one or more supplemental sensors that are configured to measure non-optical characteristics of the fluid sample under analysis. For example, the fluorometer may include a temperature sensor, a pH sensor, an electrical conductivity sensor, a flow rate sensor, a pressure sensor, and/or any other suitable type of sensor. Such supplemental sensors may have sensor interfaces located on the external surface of the fluorometer housing, e.g., adjacent the optical lens of the fluorometer, with sensor electronics positioned inside the housing. The supplemental sensors can measure non-optical properties of substantially the same portion of fluid being optically analyzed by the fluorometer. By measuring both optical and non-optical properties of the fluid under analysis, a process utilizing the fluid may be benchmarked and controlled more accurately than if only optical or non-optical properties of the fluid were measured.

In one example, an optical sensor is described that includes a housing, a first optical emitter, a second optical emitter, and an optical detector. According to the example, the housing defines an optical pathway configured to direct light through a lens optically coupled to the optical pathway into a fluid sample and to receive light from the fluid sample. The first optical emitter is configured to emit light at a first wavelength through the optical pathway into the sample. The second optical emitter is configured to emit light at a second wavelength through the optical pathway into the sample. In addition, the optical detector is configured to receive light from the fluid sample through the optical pathway.

In some embodiments, the first and second wavelengths are such that the first wavelength excites fluorescence in the sample while the second wavelength scatters off the sample. The detector can detect the fluoresced light from the sample in order to determine a characteristic of the sample, such as the concentration of a fluorophore. In some embodiments, the detector also measures the scattered light from the sample in order to determine another property of the sample which may have an effect on the fluorescence thereof, such as the turbidity of the sample. The amount of scattered light detected in these examples can be used to adjust the amount of fluorescent light detected and, correspondingly, any fluid characteristics determined based on the detected fluorescent emissions. For example, a highly turbid fluid sample may generate fewer fluorescent emissions than a less turbid fluid sample, even though the highly turbid fluid sample has a higher concentration of fluorophores. This can occur if the turbidity in the fluid sample blocks fluorescent emissions that would otherwise be detected by the fluorometer. Accordingly, with knowledge of the turbidity of the fluid sample, the fluorescent emission detected from the fluid sample can be adjusted accordingly.

An optical sensor according to the disclosure can have a number of different detector configurations. In one example, the optical sensor includes a single optical detector that receives fluorescent emissions emitted from a fluid sample under analysis and also receives light scattered from the fluid sample under analysis. The optical detector may receive the light through a single optical lens mounted on an external surface of the optical detector housing. In such examples, the optical sensor may alternatingly emit light from the first optical emitter configured to generate fluorescent emissions while the second optical emitter configured to generate scattered light is off and then emit light from the second optical emitter while the first optical emitter is off. In such examples, the single optical detector may alternatingly receive fluorescent emissions emitted from the fluid sample in response to light from the first optical emitter and light scattered from the fluid sample in response to light from the second optical emitter, providing different detection channels for the same optical detector. In other examples, the optical sensor includes multiple optical detectors, including one optical detector configured to measure fluorescent emissions emitted from a fluid sample in response to light from the first optical emitter and a second optical detector configured to measure light scattered from the fluid sample in response to light from the second optical emitter. The first and second optical emitters may emit light into the fluid sample simultaneously in these examples.

In some additional examples, the optical sensor includes a reference detector configured to measure light from the first and second optical emitters prior to their being incident on the sample. In this way, the amount of light incident on the sample to cause scattering and fluorescence can be determined. This information can be used to scale the detected scattered and fluoresced light, as the amount of light scattered and fluoresced is generally a function of the amount of light incident on the sample. Accordingly, when used, the reference detector can act to calibrate the detector and provide a reference point for the measurements made by the first optical detector.

In various embodiments, the optical sensor includes an optical pathway through which light is guided from the optical emitters to the sample and guided back from the sample to the optical detector. Various optical components including partially reflective optical windows and filters can direct light toward its desired destination while preventing unwanted light from interfering with measurements. Additional optical pathways may be provided to guide light to and from these optical components. For example, in some embodiments, the optical sensor includes a partially reflective optical window that functions to direct portions of light from the first and second optical emitters both to the second optical detector (e.g., reference detector) and toward the optical pathway. In these embodiments, another partially reflective optical window may direct portions of the light from each emitter toward the sample via the optical pathway. In some embodiments, light scattered and/or fluoresced from the sample travel back through the optical pathway and are transmitted through the partially reflective optical window toward the first optical detector.

In one example, a system is described that includes an optical sensor and a controller. The optical sensor includes a housing having an optical pathway configured to direct light through a lens optically connected to the optical pathway into a fluid sample under analysis and receive light from the fluid sample through the lens. The optical sensor also includes a first optical emitter, a second optical emitter, and an optical detector. According to the example, the controller is configured to control the first optical emitter to emit light at a first wavelength through the optical pathway into the fluid sample under analysis, detect fluorescent emissions emitted by the fluid sample and received through the optical pathway via the optical detector, control the second optical emitter to emit light at a second wavelength different than the first wavelength through the optical pathway and into the fluid sample under analysis, and detect light scattered by the fluid sample and received through the optical pathway by the optical detector.

In another example, a method is described including emitting light at first wavelength by a first optical emitter through an optical pathway into a fluid sample, and receiving fluorescent emissions emitted by the fluid sample through the optical pathway by an optical detector. The method further includes emitting light at a second wavelength different than the first wavelength by a second optical emitter through the optical pathway and into the fluid sample, and receiving light scattered by the fluid sample through the optical pathway by the optical detector. Various methods include emitting both the first and second wavelengths of light simultaneously, or alternatively, alternatingly. In some embodiments, receiving light fluoresced by the sample is done while emitting light from the first optical emitter, while in alternative embodiments it is done subsequent to ceasing emission from the first optical emitter.

The details of one or more examples are set forth in the accompanying drawings and the description below. Other features, objects, and advantages will be apparent from the description and drawings, and from the claims.

DETAILED DESCRIPTION

Figure 1:
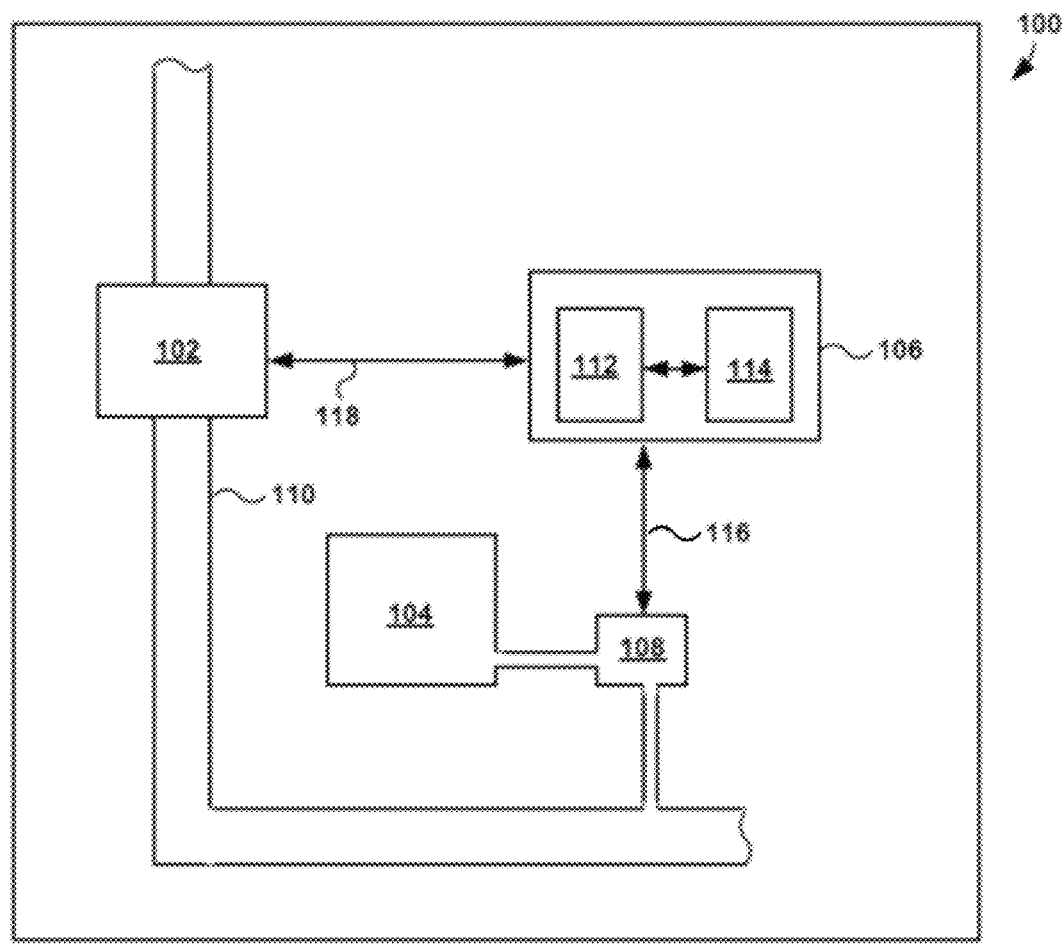
FIG. 1 is a diagram illustrating an example fluid system that may include an optical sensor according to examples of the disclosure.

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Optical sensors are used in a variety of applications, including monitoring industrial processes. An optical sensor can be implemented as a portable, hand-held device that is used to periodically analyze the optical characteristics of a fluid in an industrial process. Alternatively, an optical sensor can be installed online to continuously analyze the optical characteristics of a fluid in an industrial process. In either case, the optical sensor may optically analyze the fluid sample and determine different characteristics of the fluid, such as the concentration of one or more chemical species in the fluid.

As one example, optical sensors are often used in industrial cleaning and sanitizing applications. During an industrial cleaning and sanitizing process, water is typically pumped through an industrial piping system to flush the piping system of product residing in pipes and any contamination build-up inside the pipes. The water may also contain a sanitizing agent that functions to sanitize and disinfect the piping system. The cleaning and sanitizing process can prepare the piping system to receive new product and/or a different product than was previously processed on the system.

An optical sensor can be used to monitor the characteristics of flushing and/or sanitizing water flowing through a piping system during an industrial cleaning and sanitizing process. Either continuously or on an intermittent basis, samples of water are extracted from the piping system and delivered to the optical sensor. Within the optical sensor, light is emitted into the water sample and used to evaluate the characteristics of the water sample. The optical sensor may determine whether residual product in the piping system has been sufficiently flushed out of the pipes, for example, by determining that there is little or no residual product in the water sample. The optical sensor may also determine the concentration of sanitizer in the water sample, for example, by measuring a fluorescent signal emitted by the sanitizer in response to the light emitted into the water sample. If it is determined that there is an insufficient amount of sanitizer in the water sample to properly sanitize the piping system, the amount of sanitizer is increased to ensure proper sanitizing of the system.

While the optical sensor can have a variety of different configurations, in some examples, the optical sensor is designed to have a single optical lens through which light is emitted into a fluid sample and also received from the fluid sample. The optical sensor may include a housing that contains various electronic components of the sensor and also has optical pathways to control light movement to and from the single optical lens. Such an arrangement may facilitate design of a compact optical sensor that can be readily installed through a variety of mechanical pipe and process fittings to optically analyze a desired process fluid.

FIG. 1 is a conceptual diagram illustrating an example fluid system 100, which may be used to produce a chemical solution having fluorescent properties, such as a sanitizer solution exhibiting fluorescent properties. Fluid system 100 includes optical sensor 102, a reservoir 104, a controller 106, and a pump 108. Reservoir 104 may store a concentrated chemical agent that can be blended with a diluent, such as water, to generate the chemical solution, or can be any other source for the sample to be characterized. Optical sensor 102 is optically connected to fluid pathway 110 and is configured to determine one or more characteristics of the solution traveling through the fluid pathway.

The fluid pathway 110 can be a single fluid vessel or combination of vessels which carry a fluid sample through the fluid system 100 including, but not limited to, pipes, tanks, valves, pipe tees and junctions, and the like. In some instances, one or more components of the fluid pathway 110 can define an interface or opening sized to receive or otherwise engage with the optical sensor 102. In operation, optical sensor 102 can communicate with controller 106, and controller 106 can control fluid system 100 based on the fluid characteristic information generated by the optical sensor.

Controller 106 is communicatively connected to optical sensor 102 and pump 108. Controller 106 includes processor 112 and memory 114. Controller 106 communicates with pump 108 via a connection 116. Signals generated by optical sensor 102 are communicated to controller 106 via a wired or wireless connection, which in the example of FIG. 1 is illustrated as wired connection 118. Memory 109 stores software for running controller 106 and may also store data generated or received by processor 112, e.g., from optical sensor 102. Processor 112 runs software stored in memory 114 to manage the operation of fluid system 100.

As described in greater detail below, optical sensor 102 is configured to optically analyze a sample of fluid flowing through fluid pathway 110. Optical sensor 102 may include an optical detector that is positioned and configured to measure fluorescent emissions emitted by the fluid sample. In some configurations, a single optical detector can be used to measure both scattering and fluorescence from a sample and can receive both scattered and fluoresced light via a single optical pathway in the sensor 102. The single optical pathway can additionally be used to direct light to induce scattering and fluorescence to the sample, thereby providing a compact and spatially efficient interface between the sensor 102 and the sample. Providing a single optical communication point between the sensor 102 and sample also can simplify implementation of the sensor 102 into fluid system 100, e.g., by providing a sensor that can easily interface with one or more components of the fluid pathway 110 such as a tee configuration in a pipe.

In the example of FIG. 1, fluid system 100 is configured to generate or otherwise receive a chemical solution having fluorescent properties. Fluid system 100 can combine one or more concentrated chemical agents stored within or received from reservoir 104 with water or another diluting fluid to produce the chemical solutions. In some instances, dilution is not necessary, as the reservoir immediately provides an appropriate sample. Example chemical solutions that may be produced by fluid system 100 include, but are not limited to, cleaning agents, sanitizing agents, cooling water for industrial cooling towers, biocides such as pesticides, anti-corrosion agents, anti-scaling agents, anti-fouling agents, laundry detergents, clean-in-place (CIP) cleaners, floor coatings, vehicle care compositions, water care compositions, bottle washing compositions, and the like.

The chemical solutions generated by or flowing through the fluid system 100 may emit fluorescent radiation in response to optical energy directed into the solutions by optical sensor 102. Optical sensor 102 can then detect the emitted fluorescent radiation and determine various characteristics of the solution, such as a concentration of one or more chemical compounds in the solution, based on the magnitude of the emitted fluorescent radiation. In some embodiments, the optical sensor 102 can direct optical energy to the solution and receive fluorescent radiation from the solution via an optical pathway within the optical sensor 102, allowing for a compact design for the optical sensor 102.

In order to enable optical sensor 102 to detect fluorescent emissions, the fluid generated by fluid system 100 and received by optical sensor 102 may include a molecule that exhibits fluorescent characteristics. In some examples, the fluid includes a polycyclic compound and/or a benzene molecule that has one or more substituent electron donating groups such as, e.g., —OH, —NH$_2$, and —OCH$_3$, which may exhibit fluorescent characteristics. Depending on the application, these compounds may be naturally present in the chemical solutions generated by fluid system 100 because of the functional properties (e.g., cleaning and sanitizing properties) imparted to the solutions by the compounds.

In addition to or in lieu of a naturally fluorescing compound, the fluid generated by fluid system 100 and received by optical sensor 102 may include a fluorescent tracer (which may also be referred to as a fluorescent marker). The fluorescent tracer can be incorporated into the fluid specifically to impart fluorescing properties to the fluid. Example fluorescent tracer compounds include, but are not limited to, naphthalene disulfonate (NDSA), 2-naphthalenesulfonic acid, Acid Yellow 7,1,3,6,8-pyrenetetrasulfonic acid sodium salt, and fluorescein.

Independent of the specific composition of the fluid generated by fluid system 100, the system can generate fluid in any suitable fashion. Under the control of controller 106, pump 108 can mechanically pump a defined quantity of concentrated chemical agent out of reservoir 104 and combine the chemical agent with water to generate a liquid solution suitable for the intended application. Fluid pathway 110 can then convey the liquid solution to an intended discharge location. In some examples, fluid system 100 may generate a flow of liquid solution continuously for a period of time such as, e.g., a period of greater than 5 minutes, a period of greater than 30 minutes, or even a period of greater than 24 hours. Fluid system 100 may generate solution continuously in that the flow of solution passing through fluid pathway 110 may be substantially or entirely uninterrupted over the period of time.

In some examples, monitoring the characteristics of the fluid flowing through fluid pathway 110 can help ensure that the fluid is appropriately formulated for an intended downstream application. Monitoring the characteristics of the fluid flowing through fluid pathway 110 can also provide feedback information, e.g., for adjusting parameters used to generate new fluid solution. For these and other reasons, fluid system 100 can include a sensor to determine various characteristics of the fluid generated by the system. The sensor can engage directly with the fluid pathway 110 to monitor fluid characteristics, or can alternatively receive fluid from the fluid system 100 separately from the fluid pathway 100.

In the example of FIG. 1, fluid system 100 includes optical sensor 102. The optical sensor 102 can engage the fluid pathway 110 in any number of ways, such as interfacing with a tee configuration in a pipe in the fluid pathway 110, being inserted into a port of a tank or other fluid vessel through which fluid periodically flows, or the like. Optical sensor 102 may determine one or more characteristics of the fluid flowing through fluid pathway 110. Example characteristics include, but are not limited to, the concentration of one or more chemical compounds within the fluid (e.g., the concentration of one or more active agents added from reservoir 104 and/or the concentration of one or more materials being flushed from piping in fluid system 100), the temperature of the fluid, the conductivity of the fluid, the pH of the fluid, the flow rate at which the fluid moves through the optical sensor, and/or other characteristics of the fluid that may help ensure the system from which the fluid sample being analyzed is operating properly. Optical sensor 102 may communicate detected characteristic information to controller 106 via connection 118.

Optical sensor 102 may be controlled by controller 106 or one or more other controllers within fluid system 100. For example, optical sensor 102 may include a device controller (not illustrated in FIG. 1) that controls the optical sensor to emit light into the fluid under analysis and also to detect light received back from the fluid. The device controller may be positioned physically adjacent to the other components of the optical sensor, such as inside a housing that houses a light source and detector of the optical sensor. In such examples, controller 106 may function as a system controller that is communicatively coupled to the device controller of optical sensor 102. The system controller 106 may control fluid system 106 based on optical characteristic data received from and/or generated by the device controller. In other examples, optical sensor 102 does not include a separate device controller but instead is controlled by controller 106 that also controls fluid system 100. Therefore, although optical sensor 102 is generally described as being controlled by controller 106, it should be appreciated that fluid system 100 may include one or more controllers (e.g., two, three, or more), working alone or in combination, to perform the functions attributed to optical sensor 102 and controller 106 in this disclosure. Devices described as controllers may include processors, such as microprocessors, digital signal processors (DSPs), application specific integrated circuits (ASICs), field programmable gate arrays (FPGAs), or any other equivalent integrated or discrete logic circuitry, as well as any combinations of such components.

In the example illustrated in FIG. 1, processor 112 of controller 106 can receive determined optical characteristic information from optical sensor 102 and compare the determined characteristic information to one or more thresholds stored in memory 114, such as one or more concentration thresholds. Based on the comparison, controller 106 may adjust fluid system 100, e.g., so that the detected characteristic matches a target value for the characteristic. In some examples, controller 106 starts and/or stops pump 108 or increases and/or decreases the rate of pump 108 to adjust the concentration of a chemical compound flowing through fluid pathway 110. Starting pump 108 or increasing the operating rate of pump 108 can increase the concentration of the chemical compound in the fluid. Stopping pump 108 or decreasing the operating rate of pump 108 can decrease the concentration of chemical compound in the fluid. In some additional examples, controller 106 may control the flow of water that mixes with a chemical compound in reservoir 104 based on determined characteristic information, for example, by starting or stopping a pump that controls the flow of water or by increasing or decreasing the rate at which the pump operates. Although not illustrated in the example fluid system 100 of FIG. 1, controller 106 may also be communicatively coupled to a heat exchanger, heater, and/or cooler to adjust the temperature of fluid flowing through fluid pathway 110 based on characteristic information received from optical sensor 102.

In yet other examples, optical sensor 102 may be used to determine one or more characteristics of a stationary volume of fluid that does not flow through a flow chamber of the optical sensor. For example, optical sensor 102 may be implemented as an offline monitoring tool (e.g., as a handheld sensor), that requires filling the optical sensor with a fluid sample manually extracted from fluid system 100. Alternatively, the optical sensor 102 can engage a portion of the fluid system 100 configured to receive and hold a stationary volume of the fluid, such as a stop-flow device, or an otherwise external vessel for receiving fluid and engaging the optical sensor 102. In some embodiments, a controller 106 can control a system of pumps and/or valves to direct a finite amount of the sample to be measured into such a stationary vessel outfitted with a sensor 102.

Fluid system 100 in the example of FIG. 1 also includes reservoir 104, pump 108, and fluid pathway 110. Reservoir 104 may be any type of container that stores a chemical agent for subsequent delivery including, e.g., a tank, a tote, a bottle, and a box. Reservoir 104 may store a liquid, a solid (e.g., powder), and/or a gas. Pump 108 may be any form of pumping mechanism that supplies fluid from reservoir 104. For example, pump 108 may comprise a peristaltic pump or other form of continuous pump, a positive-displacement pump, or any other type of pump appropriate for the particular application. In examples in which reservoir 104 stores a solid and/or a gas, pump 108 may be replaced with a different type of metering device configured to deliver the gas and/or solid chemical agent to an intended discharge location. Fluid pathway 110 in fluid system 100 may be any type of flexible or inflexible tubing, piping, or conduit.

Figure 2:
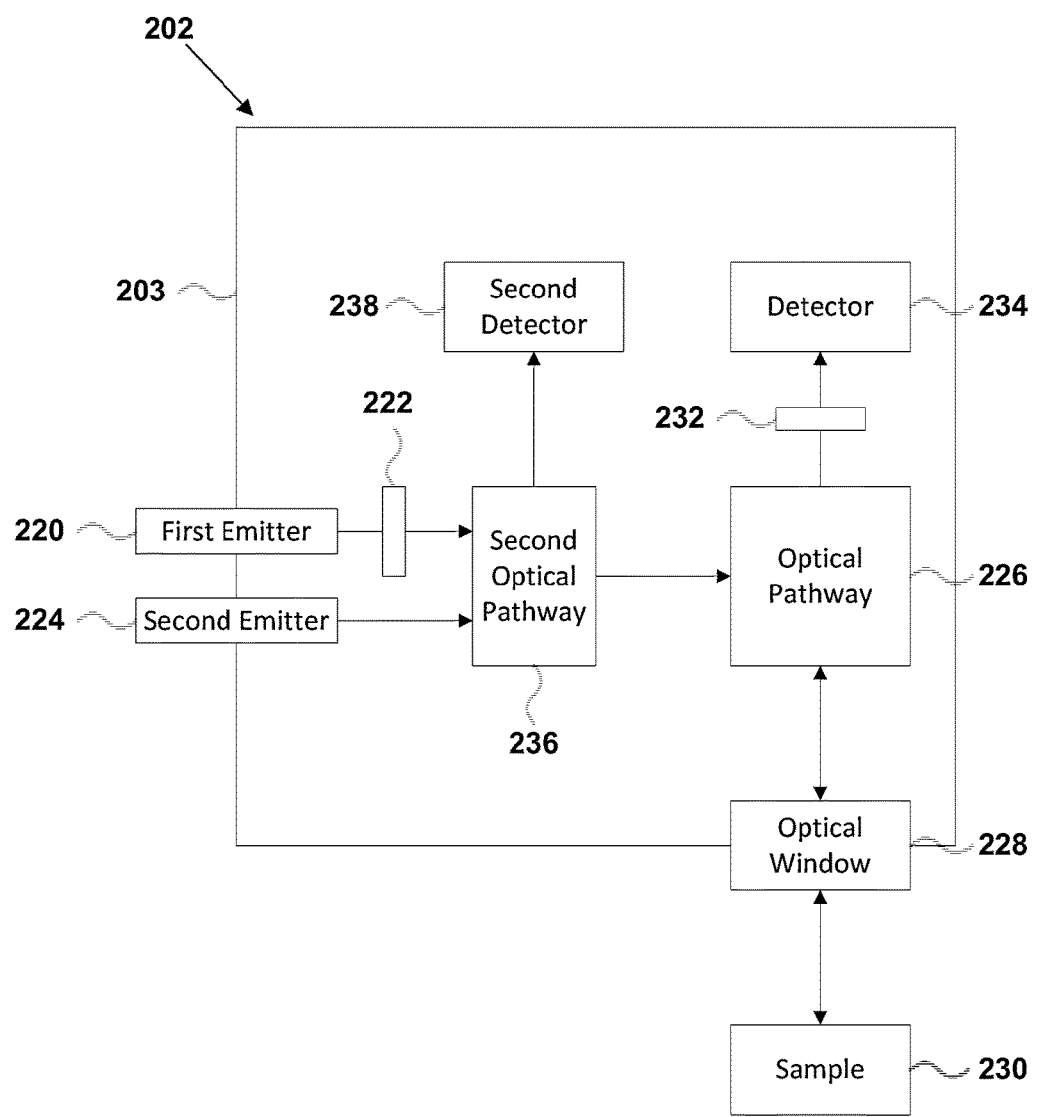
FIG. 2 is a block diagram of an example optical sensor that can determine at least one characteristic of a fluid sample.

In the example of FIG. 1, optical sensor 102 determines a characteristic of the fluid flowing through fluid pathway 110 (e.g., concentration of a chemical compound, temperature or the like) and controller 106 controls fluid system 100 based on the determined characteristic and, e.g., a target characteristic stored in memory 114. FIG. 2 is a block diagram of an example optical sensor 202 that can be installed in fluid system 100 to monitor a characteristic of a fluid flowing through fluid pathway 110. Sensor 202 may be used as optical sensor 102 in fluid system 100, or sensor 202 may be used in other applications beyond fluid system 100.

In the example of FIG. 2, the sensor 202 includes a housing 203, a first optical emitter 220, a second optical emitter 224, an optical window 228, and an optical detector 234. The housing 203 houses the first optical emitter 220, the second optical emitter 224, and the optical detector 234. Optical window 228 is positioned on an external surface of the housing 203 to provide a fluid-tight, optically transmissive barrier between an interior of the housing and fluid in fluid sample 230 that contacts the external surface of the housing. In operation, first optical emitter 220 and second optical emitter 224 emit light that is directed through optical window 228 and into the fluid sample 230 under analysis. In response to light emitted by the first optical emitter 222 and/or the second optical emitter 224 impinging on the fluid adjacent optical window 228, the fluid may scatter light and/or generate fluorescent emissions. The scattered light and/or fluorescent emissions can pass through optical window 228 to be detected by optical detector 234.

To control light transmission to and from optical window 228, optical sensor 202 includes at least one optical pathway 226 optically connecting various components of the optical sensor to the fluid sample 230 under analysis. The optical pathway 226 may guide light emitted by the first optical emitter 220 and second optical emitter 224 so the light is guided from the optical emitters, through optical lens 228, and into fluid sample 230. The optical pathway 226 may also guide light received from the fluid sample 230 through optical window 228 so the light is guided to the optical detector 234. When so configured, the first optical emitter 220 and the second optical emitter 224 may be positioned inside of the housing 203 to direct light into the optical pathway 226 and the optical detector 234 may be positioned inside of the housing to receive light from the optical pathway. Such an arrangement may allow optical sensor 202 to be configured with a single optical lens through which multiple light sources emit light and through which light is also received and detected from a fluid sample under analysis. This may help minimize the size of optical sensor 202, for example, so that the sensor is sufficiently compact to be inserted through a mechanical pipe fitting into a piece of process equipment containing fluid for analysis.

Optical sensor 202 can include any suitable number of optical pathways optically connecting various emitter and detector components housed inside the housing 203 to the fluid sample under analysis via optical window 228. In the example of FIG. 2, optical sensor 202 is conceptually illustrated as having a first optical pathway 226 and a second optical pathway 236. The second optical pathway 236 is optically connected to the first optical pathway 226 and also optically connected to the first optical emitter 220 and the second optical emitter 224. The second optical pathway 236 can receive light from the first optical emitter 220 and second optical emitter 224 and guide the light to the first optical pathway 226 which, in turn, guides the light through optical window 228 into the fluid sample 230 under analysis. By configuring optical sensor 202 with additional optical pathways, various light emitters and detectors in the optical sensor can be optically connected to the fluid sample under analysis without being positioned directly adjacent the first optical pathway 226.

Optical pathways in optical sensor 202 may be channels, segments of optically conductive tubing (e.g., fiber optic lines), or ducts that allow light to be conveyed through the optical sensor. The optical pathways may also be machined or cast into the housing 203 of the optical sensor. In different examples, the optical pathways may or may not be surrounded by optically opaque material, e.g., to bound light movement through the optical pathways and to prevent light from escaping through the sides of the optical pathways. When optical sensor 202 includes multiple optical pathways, the intersection of one optical pathway with another optical pathway may be defined where light traveling linearly through the one optical pathway is required to change direction to travel through the other optical pathway.

In the example of FIG. 2, the optical sensor 202 includes at least one light source, and, in the illustrated example, is shown with two light sources: first optical emitter 220 and second optical emitter 224. Each of the first optical emitter 220 and the second optical emitter 224 is a light source and can be implemented using any appropriate light source, such as a laser, a lamp, an LED, or the like. In some embodiments, the first optical emitter 220 and/or the second optical emitter 224 are configured to emit substantially uncollimated beams of light into the optical pathway 226. In this case, the optical sensor 202 can include optical components to collimate the light from the first optical emitter 220 and/or the second optical emitter 224 in order to achieve a higher optical efficiency during operation.

Configuring the optical sensor 202 with multiple light sources may be useful, for example, to emit light at different wavelengths into the fluid sample 230. For example, the first optical emitter 220 may be configured to emit light within a first range of wavelengths into the fluid sample 230 to generate fluorescent emissions within the fluid. The second optical emitter 224 may be configured to emit light within a second range of wavelengths different than the first range of wavelengths to measure the amount of light scattered by fluid sample 230.

Independent of the specific number of light sources included in optical sensor 202, the optical sensor includes an optical window 228 through which light is directed into and received from the fluid sample 230. In some examples, optical window 228 focuses light directed into and/or received from the fluid sample under analysis. In such examples, optical window 228 may be referred to as an optical lens. In other examples, optical window 228 passes light directed into and/or received from the fluid sample without focusing the light. Therefore, although optical window 228 is also referred to as optical lens 228 in this disclosure, it should be appreciated that an optical sensor in accordance with the disclosure can have an optical window that does or does not focus light.

Optical window 228 is optically connected to optical pathways 226 and, in some examples, physically connected at a terminal end of the optical pathway. In different examples, the optical window 228 is formed of a single lens or a system of lenses able to direct light into and receive light from the fluid sample 230. The optical window 228 can be integral (permanently attached) to the housing 203 or can be removable from the housing. In some examples, optical window 228 is an optical lens formed by a ball lens positioned within optical pathway 226 to seal the optical pathway and prevent fluid from fluid sample 230 from entering the optical pathway. In such examples, the ball lens may extend distally from an external face of the housing 203, e.g., into a moving flow of fluid. The optical lens 228 can be fabricated from glass, sapphire, or other suitable optically transparent materials.

As briefly mentioned above, the optical pathway 226 is configured to direct light through an optical window 228 optically connected to the optical pathway and also to receive light from the fluid sample through the optical window 228. To detect the light received from the fluid sample under analysis, optical sensor 202 includes at least one optical detector 234 optically connected to optical pathway 226. The optical detector 234 can be implemented using any appropriate detector for detecting light, such as a solid-state photodiode or photomultiplier, for example. The optical detector 234 may be sensitive to, and therefore detect, only a narrow band of wavelengths. Alternatively, the optical detector 234 may be sensitive to, and therefore detect, a wide range of light wavelengths.

During operation, light is emitted into the fluid sample 230 via the optical window 228 optically connected to the optical pathway 226. The window 228 can additionally collect light from the fluid sample 230, such as light scattered off of the sample or emitted by the sample via a mechanism such as fluorescence. Such light can be directed from the fluid sample 230 back into the optical pathway 226 via the window 228 and received by optical detector 234.

To control the wavelengths of light emitted by the optical emitters and/or detected by the optical detector in sensor 202, the optical sensor may include an optical filter. The optical filter can filter wavelengths of light emitted by the optical emitters and/or received by optical detectors, e.g., so that only certain wavelengths of light are emitted into fluid sample 230 and/or received from the fluid sample and detected by optical detector 234.

For example, the sensor 202 may include an optical filter 232 configured to prevent unwanted light received from fluid sample 230 from impinging on the optical detector 234. If the detection of a particular wavelength or band of wavelengths is desired but the optical detector 234 is sensitive to a wider band or otherwise large number of wavelengths, the filter 232 can act to prevent light outside of the desired band from impinging on the optical detector 234. The filter 232 can absorb or reflect light that it does not allow to pass through.

According to some embodiments, one of the first optical emitter 220 and second optical emitter 224 may emit a wider band of wavelengths than is desired or useful for use with the sensor 202, as will be explained in more detail below. Accordingly, sensor 202 can include a filter 222 disposed between the first 220 and/or the second 224 optical emitter and the fluid sample 230. The filter 222 may be configured to prevent certain wavelengths of light from reaching the fluid sample 230 via the optical pathway 226. Such a filter 222 can be positioned to at least partially filter light from either one or both of the first optical emitter 220 and the second optical emitter 224. For example, in FIG. 2, the optical filter 222 is shown disposed between the first optical emitter 220 and the second optical pathway 236.

During operation, the optical sensor 202 can control the first optical emitter 220 to emit light at a first wavelength (e.g., range of wavelengths) into the fluid sample 230, control the second optical emitter 224 to emit light at a second wavelength (e.g., range of wavelengths) into the fluid sample, and receive light from the fluid sample at optical detector 234. According to some embodiments, the first optical emitter 220 is configured to emit light at a wavelength sufficient to cause molecules in the fluid sample 230 under analysis to fluoresce. Light fluoresced by the fluid sample 230 may be collected by the optical window 228 and directed into the optical pathway 226 as an emission beam. Additionally, the second optical emitter 224 may be configured to emit light at a wavelength sufficient to cause light scattering by the fluid sample 230 under analysis. Such light scattering may occur when the fluid sample 230 is turbid, e.g., and contains light reflective particles. Light scattered by the fluid sample 230 may be collected by optical window 228 and directed back into the optical pathway 226 as a scattering beam.

Although the wavelengths can vary, in some examples, the first optical emitter 220 is configured to emit light within a wavelength ranging from approximately 225 nanometers (nm) to approximately 700 nm, such as from approximately 250 nm to approximately 350 nm, or from approximately 265 nm to approximately 290 nm. The second optical emitter 224 may emit light at a wavelength ranging from approximately 750 nm to approximately 1200 nm, such as from approximately 800 nm to approximately 900 nm. For example, the first optical emitter 220 may emit light within the ultraviolet (UV) spectrum while the second optical emitter 224 emits light within the infrared (IR) spectrum. Other wavelengths are both contemplated and possible, and it should be appreciated that the disclosure is not limited in this respect.

To detect light emanating from the fluid sample 230 under analysis (e.g., fluorescent emissions, light scattering), the sensor 202 of FIG. 2 further includes an optical detector 234. Optical detector 234 is optically connected to optical pathway 226 and may receive at least a portion of the fluorescent emission beam and the scattered light beam transmitted through the optical window 228 from the fluid sample 230 under analysis. Upon entering housing 203, the received portions of the fluorescent emission beam and scattered light beam may be directed to the optical detector via the optical pathway 226 for measurement and/or analysis. In some embodiments, the intensities of the beams are measured by the optical detector 234 and used to determine information about the sample, such as the concentration of a particular component (e.g., a fluorescing compound and/or a non-fluorescing compound) contained therein. Information about the fluid sample under analysis carried by scattered light and fluorescent emissions received from the fluid sample and detected by optical detector 234 may provide different channels of information, e.g., for characterizing the fluid sample and/or controlling the system containing the fluid sample.

For example, the optical sensor 202 may use light scattering information detected by optical detector 234 to adjust or correct the amount of fluorescent emissions detected by the optical sensor and/or calculations based on the measured fluorescent emissions. The turbidity of the fluid sample under analysis may affect the magnitude of the fluorescent emissions generated by the fluid sample and/or received by optical detector 234. Optical sensor 202 may compensate for these turbidity effects by measuring the amount of turbidity in the fluid sample, which may be proportional to the amount of light scattered by the fluid sample, and adjusting the magnitude of the measured fluorescent emissions based on the turbidity measurement. In addition, optical detector 234 may measure the amount of light scattered by the fluid sample 230 in response to light emitted by the second optical emitter 224 and determine other characteristics of the fluid sample. For example, the optical sensor 202 may determine a concentration of a non-fluorescing species (e.g., a contaminant) in the fluid sample based on the amount of light scattered by the fluid sample and, e.g., calibration data stored in memory. For instance, if the fluid sample 230 under analysis has a first concentration of a non-fluorescing chemical compound(s), the optical detector 234 may detect a first magnitude of scattered light. However, if the fluid sample has a second concentration of the non-fluorescing chemical compound(s) that is greater than the first concentration, the optical detector 234 may detect a second magnitude of scattered light that is greater than the first magnitude.

Optical sensor 202 includes at least one, and optionally multiple, optical detectors to detect light received from the fluid sample 230 in response to light emitted by the first optical emitter 220 and/or the second optical emitter 224. To measure the amount of light emitted by the first optical emitter 220 and/or the second optical emitter 224 into the fluid sample 230 under analysis, optical sensor 202 may also include at least one reference detector. The reference detector may be positioned inside of the housing 203 and configured to measure light emitted by the first optical emitter 220 and/or the second optical emitter 224. The amount of light received from the fluid sample 230 in response to light emitted by the first optical emitter 220 and/or the second optical emitter 224 may vary based on the amount of light originally emitted by the first and second optical emitters. Accordingly, light measurements made by the reference detector can be used to adjust light measurements made by optical detector 234.

In the embodiment of FIG. 2, optical sensor 202 includes a second optical detector 238 that can function as a reference detector. Second optical detector 238 is in optical communication with the second optical pathway 236 and is configured to receive light therefrom. In some embodiments, the second optical detector 238 is configured to receive light from both the first optical emitter 220 and the second optical emitter 224, e.g., in alternating sequence. Such light can be measured at the second optical detector 238 in order to determine operating conditions of the sensor, calibrate the sensor, or to perform any other useful function associated with the sensor. In an exemplary embodiment, the second optical detector 238 can detect light received from the first optical emitter 220 and then detect light received from the second optical emitter 224. Optical sensor 202 may then determine the relative intensities or an intensity ratio between light emitted from the two optical emitters. This information can be used to supplement the information determined about the fluid sample under analysis, such as adjusting a fluid characteristic determined based on light received by the first optical detector 234.

Optical sensor 202 is configured to measure at least one optical characteristic of the fluid sample 230 under analysis. To supplement optical characteristic information generated by the optical sensor 202, the sensor may include one or more non-optical sensors configured to measure non-optical characteristics of the fluid sample 230 under analysis. The non-optical sensor hardware/software may be housed within housing 203 and include a contact extending through an external surface of the housing (e.g., adjacent to optical lens 228) for measuring a non-optical property of the fluid sample under analysis. As examples, optical sensor 202 may include a temperature sensor, a pH sensor, an electrical conductivity sensor, and/or a flow rate sensor. When used, the temperature sensor may sense a temperature of the fluid adjacent the sensor; the pH sensor may determine a pH of the fluid adjacent the sensor; the conductivity sensor may determine an electrical conductivity of the fluid adjacent the sensor; and the flow sensor may monitor a rate of fluid flowing past the sensor. In one example, optical sensor 202 includes both a temperature sensor and an electrical conductivity sensor. Optical sensor 202 may include additional or different non-optical sensors, and the disclosure is not limited to an optical sensor that utilizes any particular type of non-optical sensor.

Figure 3:
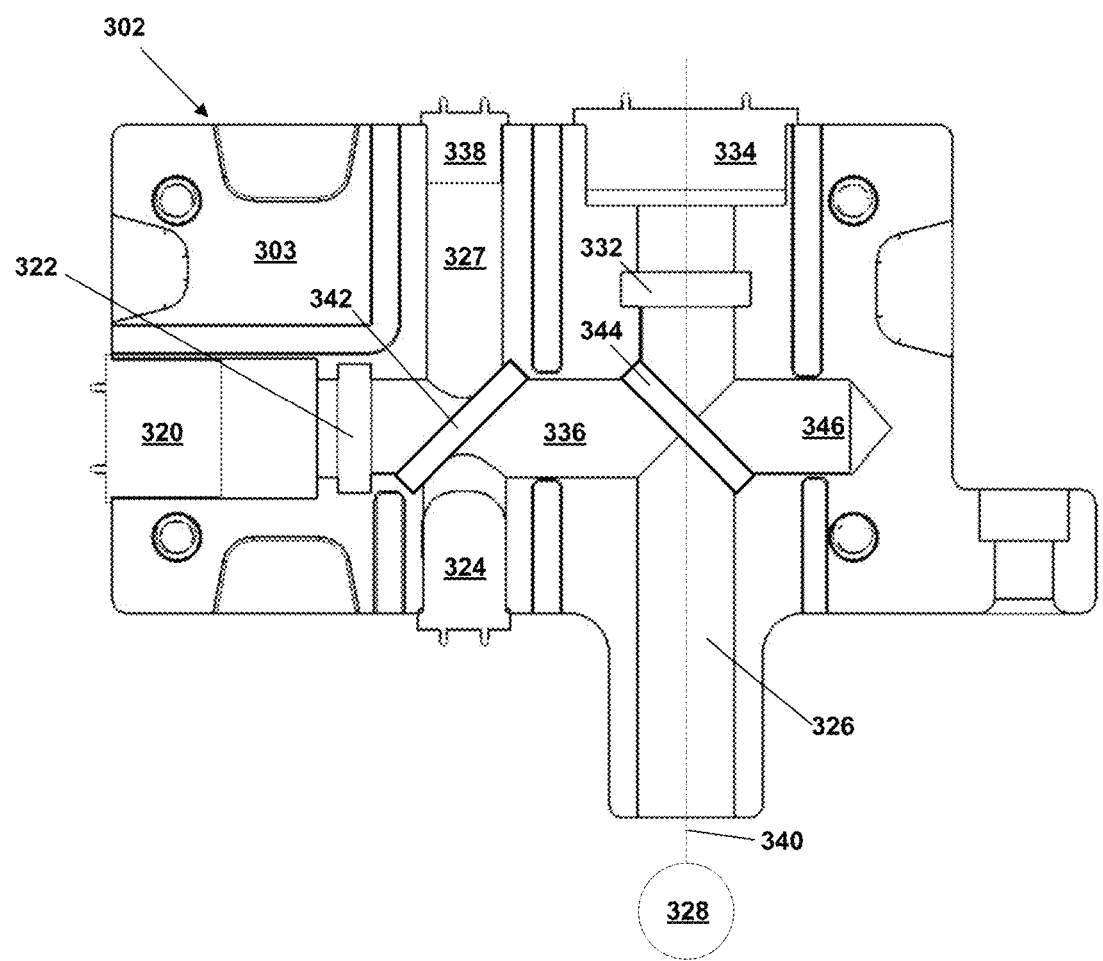
FIG. 3 is a schematic drawing of an example arrangement of components that may be used for the optical sensor of FIG. 2.

The sensor 202 of FIG. 2 can have a number of different physical configurations. FIG. 3 is a schematic drawing of an example arrangement of components that may be used for the optical sensor of FIG. 2. FIG. 3 shows a sensor 302 for measuring at least one property of a fluid sample. Similar to the sensor of FIG. 2, sensor 302 comprises a first optical emitter 320 and a second optical emitter 324. First 320 and second 324 optical emitters can include any appropriate light sources, including those discussed above with respect to FIG. 2. During operation, the first optical emitter 320 can emit light at a first wavelength while the second optical emitter 324 can emit light at a second wavelength. The first wavelength may be the same wavelength or range of wavelengths as the second wavelength, or the first wavelength may be a different wavelength or range of wavelengths as the second wavelength. Depending on the application, the first optical emitter 320 and second optical emitter 324 can emit light within the ultraviolet (UV), infrared (IR), and/or visible light spectrum. In some examples as described above, the first wavelength may cause molecules in the fluid sample under analysis (e.g., fluid sample 230) to excite and fluoresce, while the second wavelength may scatter off the fluid sample under analysis.

Additionally, the first 320 and/or second 324 optical emitter may be such that one or both emit unnecessary or unwanted light in addition to the first or second wavelengths of light desired to be emitted. To prevent such light from undesirably affecting measurements, sensor 302 may include a first optical filter 322 configured to limit the light emitted by the first optical emitter 320 into the sample under analysis. The embodiment of FIG. 3 shows a first optical filter 322 positioned between the first optical emitter 320 and a partially reflective optical window 342. The first optical filter 322 can be configured to filter out, for example, substantially all wavelengths of light within a range of fluorescent light emitted by the fluid sample, when the fluid sample emits fluorescence. Such a filter 322 can help eliminate false fluorescence detection by detector 334 in the sensor due to scattering of light within the same wavelength range as the fluorescent emissions. For example, if the first optical emitter 320 were to emit light within the wavelength of the fluorescent emissions generated by the fluid sample under analysis, the optical detector 334 may detect both fluorescent emissions generated by the fluid sample and light emitted by the first optical emitter 320 and scattered back to the optical detector 334. Optical filter 322 can filter out light emitted by the first optical detector 334 within the wavelength range of the fluorescent emissions.

The sensor 302 in the example of FIG. 3 also includes a housing 303 that houses various hardware/software components of the sensor and controls light movement through the sensor. In some embodiments, the housing 303 contains all or some of the first optical emitter 320 and/or the second optical emitter 324, while in other embodiments, the emitters are located external to the housing 303.

As was the case with the schematic sensor shown in FIG. 2, the embodiment shown in FIG. 3 includes an optical detector 334, an optical window 328 (e.g., optical lens 328) for directing light into and receiving light from a fluid sample, and an optical pathway 326. In the illustrated example, optical lens 328 is shown physically separate from but optically connected to optical pathway 326. In other examples, lens 328 is physically connected (e.g., attached) at a terminal end of the optical pathway.

To control light movement through optical sensor 302, the optical sensor includes at least one optical pathway which, in the illustrated example is shown as three optical pathways: a first optical pathway 326, a second optical pathway 336, and a third optical pathway 327. The optical pathways may define bounded channels, tubes, conduits, or cavities that control light movement through the sensor. The emitters and detectors of optical sensor 302 may be arranged around the optical pathways to direct light into the optical pathways and/or receive light from the optical pathways. For example, the first optical emitter 320 and second optical emitter 324 in FIG. 3 are configured to direct light into the first optical pathway 326 that is optically connected to the optical lens 328 and, subsequently, the fluid sample under analysis. Further, the optical detector 334 in FIG. 3 is configured to receive light from the first optical pathway 326 that emanates from the fluid sample under analysis and travels through optical lens 328.

The optical sensor 302 can have a number of different optical pathway configurations and the configurations can vary, e.g., based on the number of optical emitters and detectors contained in the sensor. In the example of FIG. 3, optical sensor 302 includes the first optical pathway 326 positioned between optical lens 328 and the first optical detector 334. Light traveling linearly through the optical lens 328 (e.g., an optical center of the lens) can travel through the first optical pathway 326 and impinge on the first optical detector 334 (e.g., an optical center of the detector). In such an example, the first optical pathway 326 may define a major axis 340 extending along the length of the pathway and extending through a center of the optical lens 328 (e.g., an optical center) and a center of the first optical detector 334 (e.g., an optical center of the detector). The first optical pathway 326 may be optically connected to a single optical window of the detector (e.g., optical lens 328) to other components housed within housing 303.

The first optical emitter 320 and the second optical emitter 324 are configured to emit light into the first optical pathway 326 and, subsequently, into the fluid sample under analysis. In some examples, the first optical emitter 320 and/or the second optical emitter 324 emit light directly into the first optical pathway 326, e.g., without emitting into an intervening optical pathway that intersects the first optical pathway. In other examples, the first optical emitter 320 and/or the second optical emitter 324 emit light into an intermediate optical pathway that is optically connected to the first optical pathway 326. That is, the first optical emitter 320 and/or the second optical emitter 324 may indirectly emit light into the first optical pathway 326.

In optical sensor 302 in FIG. 3, the first optical emitter 320 is positioned to emit light into the second optical pathway 336 that extends to the first optical pathway 326. Further, the second optical emitter 324 is positioned to emit light into the third optical pathway 327 that extends to the second optical pathway 336 which, in turn, extends to the first optical pathway 326. The second optical pathway 336 intersects the first optical pathway 326, allowing at least a portion of the light transmitting from the first optical emitter 320 and second optical emitter 324 to travel through the second optical pathway, into the first optical pathway, and through the optical lens 328. The third optical pathway 327 intersects the second optical pathway, allowing at least a portion of the light transmitting from the second optical emitter 324 to travel through the third optical pathway, into the second optical pathway, into the first optical pathway, and through the optical lens 328.

Although the configuration can vary, the second optical pathway 336 in FIG. 3 intersects the first optical pathway 326 at an approximately 90 degree angle. Further, the third optical pathway 327 intersects the second optical pathway 336 at an approximately 90 degree angle. In some examples, the third optical pathway 327 extends parallel to the first optical pathway 326, while in other examples, the third optical pathway does not extend parallel to the first optical pathway. By arranging the optical emitters and optical detectors of optical sensor 302 around intersecting optical pathways optically connected to a single optical lens 328, the sensor can provide a compact design that is easily installed in a variety of chemical and fluid processes.

In examples in which the optical sensor 302 includes intersecting optical pathways to control light movement, the optical sensor may also include optical elements (e.g., reflectors, partially reflective optical windows) that direct light received from one intersecting optical pathway into another intersecting optical pathway. The optical elements can help control the direction of light movement to optical lens 328 and/or to the optical detectors 334, 338.

In the illustrated example of FIG. 3, the sensor includes a partially reflective optical window 344 that is positioned at the intersection of the first 326 and second 336 optical pathways. The partially reflective optical window 344 is configured to reflect at least a portion of light emitted by the first optical emitter 320 and the second optical emitter 324 from the second optical pathway 336 to the first optical pathway 326. In some embodiments, the partially reflective optical window is further configured to transmit light from the fluid sample and lens 328 to the optical detector 334. Accordingly, the partially reflective optical window can be configured to both transmit and reflect portions of incident light. The angle of the partially reflective optical window 344 relative to the direction of light travel through the first optical pathway may vary, e.g., based on the angle at which the first optical pathway 326 intersects the second optical pathway 336. However, in FIG. 3 where the first optical pathway 326 intersects the second optical pathway 336 at an approximately 90 degree angle, the partially reflective optical window 344 is oriented at approximately a 45 degree angle, e.g., relative to the direction of light travel through both the first optical pathway 326 and the second optical pathway 336.

According to various embodiments, the partially reflective optical window 344 can be configured to reflect or transmit between 0% and 100% of incident light, with the reflection and transmission percentages being wavelength dependent. Any suitable optical element can be used as partially reflective optical window 344. Such a partially reflective optical window 344 can comprise, for example, a dichroic filter, or any other suitable optical component.

In operation, the partially reflective optical window 344 of FIG. 3 is configured to reflect light from the first 320 and second 324 optical emitters from the second optical pathway 336 into the first optical pathway 326 (e.g., approximately 90 degrees). This can change the direction of light emitted by the first optical emitter 320 and the second optical emitter 324 from traveling along the length of the second optical pathway 336 to traveling along the length of first optical pathway 326. While the partially reflective optical window 344 may reflect at least part of the light emitted by the first optical emitter 320 and the second optical emitter 324, e.g., into the fluid sample under analysis, the partially reflective optical window may also allow at least a portion of the light received from the fluid sample to pass through the partially reflective optical window. For example, light scattered by the fluid sample under analysis and/or fluorescent emissions generated by the fluid sample may enter into the first optical pathway 326 and at least partially transmit through the partially reflective optical window 344 (e.g., without being reflected or absorbed by the optical window) to be detected by optical detector 334. In this way, the partially reflective optical window 344 can reflect light received from the optical emitters into the fluid sample and transmit light received from the fluid sample to be detected by the optical detector 334.

In some embodiments, the sensor 302 further includes a beam dump 346, positioned opposite the partially reflective optical window 344 from the first 320 and second 324 optical emitters along the second optical pathway 336. The beam dump 346 is configured to absorb or trap any light that is incident thereon. For example, in some embodiments, any light that is transmitted from the second optical pathway 336 through the partially reflective optical window 344 will be transmitted to the beam dump 346 where it will be absorbed and prevented from being detected by optical detector 334.

Optical sensor 302 in FIG. 3 also includes a second optical detector 338, which may function as a reference detector for the sensor. The second optical detector 338 is positioned to receive light emitted by the first optical emitter 320 and the second optical emitter 324. Although the location can vary, in the illustrated example, the second optical detector 338 is positioned on an opposite side of the second optical pathway 336 from the second optical emitter 324. In particular, the second optical detector 338 is positioned at a terminal end of the third optical pathway 327, opposite the second optical emitter 324. In the exemplary embodiment illustrated in FIG. 3, the first optical emitter 320 and second optical emitter 324 are oriented substantially perpendicular to one another, with the first optical emitter 320 being approximately coaxial with the second optical pathway 336 and the second optical emitter 324 being approximately coaxial with a third optical pathway 327 and located opposite a second optical detector 338. In other examples, the second optical emitter 324 (when used) can be positioned at other locations within optical sensor 302, and it should be appreciated that the disclosure is not limited to the specific configuration of FIG. 3. As one example, the position of the first optical emitter 320 and the second optical emitter 324 may be switched so that the first optical emitter is in the position occupied by the second optical emitter shown on FIG. 3 and the second optical emitter is in the position occupied by the first optical emitter.

In examples in which optical sensor 302 includes the third optical pathway 327 intersecting the second optical pathway 336, the sensor may include a partially reflective optical window 342 that is positioned at the intersection of the second 336 and third 327 optical pathways. The partially reflective optical window 342 may be configured to reflect at least a portion of light emitted by the second optical emitter 324 from the third optical pathway into the second optical pathway 336 and also transmit at least a portion of light emitted by the second optical emitter 324 to be received by the second optical detector 338. In addition, the partially reflective optical window 342 may be configured to reflect at least a portion of light emitted by the first optical emitter 320 from the second optical pathway into the third optical pathway 327 to be received by the second optical detector 338 and also transmit at least a portion of light emitted by the first optical emitter 320 to pass through the second optical pathway 336 into the first optical pathway 326. Any suitable optical element can be used as partially reflective optical window 342. Such a partially reflective optical window 342 can comprise, for example, a dichroic filter, a quartz window, and/or a sapphire window. In some embodiments, the partially reflective optical window 342 includes an anti-reflective coating.

The angle of the partially reflective optical window 342 relative to the direction of light travel through the second optical pathway 336 may vary, e.g., based on the angle at which the second optical pathway 336 intersects the third optical pathway 327. However, in FIG. 3 where the second optical pathway 336 intersects the third optical pathway 327 at an approximately 90 degree angle, the partially reflective optical window 342 is oriented at approximately a 45 degree angle, e.g., relative to the direction of light travel through the second optical pathway 336. In particular, in the illustrated exemplary embodiment, the partially reflective optical window 342 is oriented at substantially 45° relative to the second 336 and third 327 optical pathways, as well as the first 320 and second 324 optical emitters. In this arrangement, the partially reflective optical window 342 is configured to reflect a portion of the light emitted by the first optical emitter 320 from the second optical pathway 336 into the third optical pathway 327, and to transmit at least a portion of light emitted by the second optical emitter 324 into the third optical pathway 327. The partially reflective optical window 342 shown in FIG. 3 can also act to transmit a portion of the light emitted from the first optical emitter 320 into the second optical pathway 336 toward the first optical pathway 326, and to reflect a portion of the light emitted from the second optical emitter 324 from the third optical pathway 327 into the second optical pathway 336 and toward the first optical pathway 326.

Figure 4:
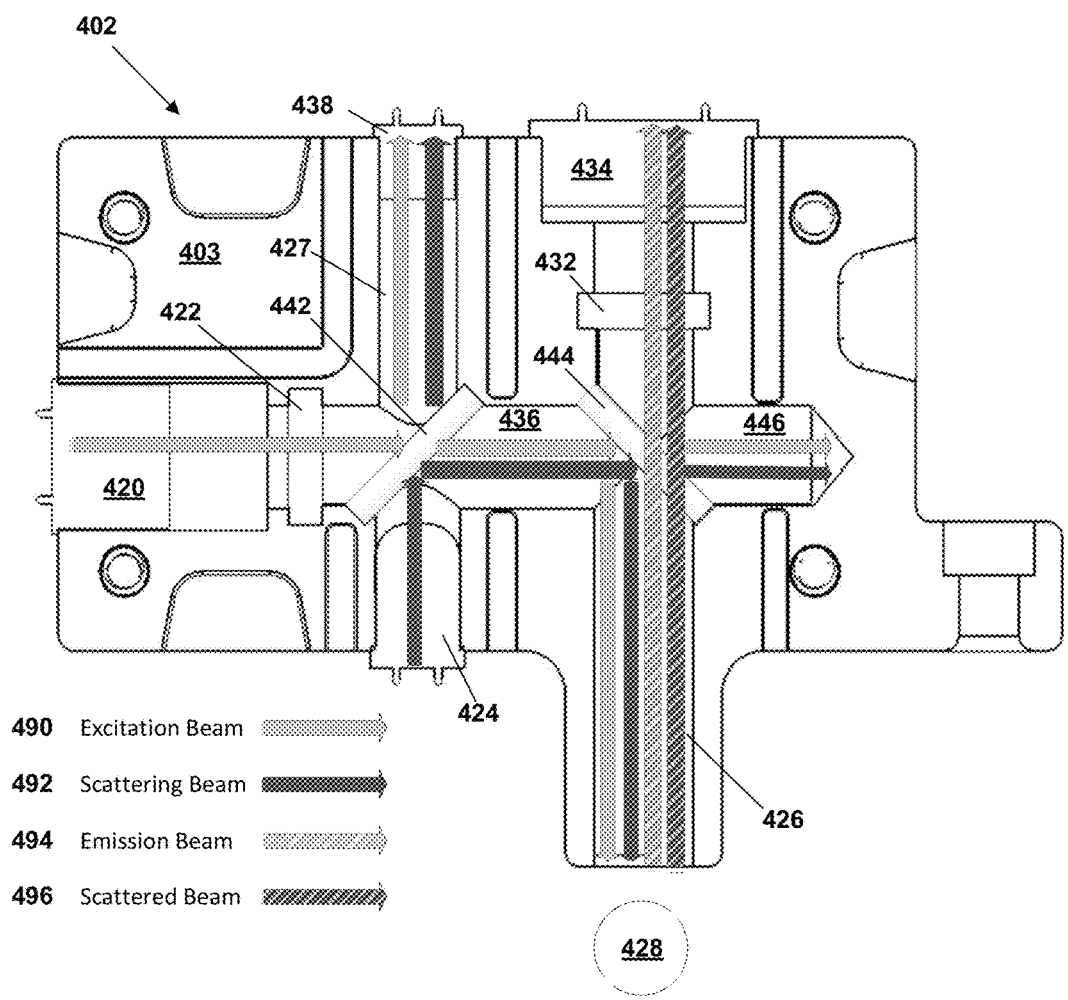
FIG. 4 is a conceptual diagram illustrating example light flows through the optical sensor of FIG. 3.

FIG. 4 is a conceptual diagram illustrating example light flows through the optical sensor illustrated in FIG. 3. For ease of description, FIG. 4 illustrates light emanating from a first optical emitter 420 and a second optical emitter 424 simultaneously and also light being received by a first optical detector 434 and a second optical detector 438 simultaneously. In practice, the first optical emitter 420 and the second optical emitter 424 may emit at the same time or at different times. Further, the first optical detector 434 and the second optical detector 438 may receive light while one or both of the first optical emitter 420 and the second optical emitter 424 are emitting or during a time period in which one or both of the emitters are not emitting light into the fluid sample under analysis. Therefore, although FIG. 4 illustrates various light flows as occurring simultaneously in sensor 402, it should be appreciated that an optical sensor according to the disclosure is not limited to such an example operation.

In the example of optical sensor 402, light is emitted from a first optical emitter 420 at a first wavelength into a second optical pathway 436. The light from the first optical emitter 420 may be configured to excite fluorescence in a fluid sample and will thus be referred to as generating an excitation beam 490 for purposes of illustration. Within sensor 402 in the example of FIG. 4, the excitation beam 490 is emitted into the second optical pathway 436 where it encounters a partially reflective optical window 442. A portion of the excitation beam 490 may be reflected by the partially reflective optical window 442 to be detected by a second optical detector 438, which may function as a reference detector. Another portion of the excitation beam 490 may pass through the partially reflective optical window 442 and continue traveling through the second optical pathway 436.

In operation, light is also emitted from a second optical emitter 424 at a second wavelength into a third optical path 427. The light from the second optical emitter 424 may be configured to scatter off the fluid sample and will thus be referred to as generating a scattering beam 492 for purposes of illustration. Within sensor 402 in the example of FIG. 4, the scattering beam 492 is emitted into the third optical pathway 427 where it encounters the partially reflective optical window 442. A portion of the scattering beam 492 may be reflected by the partially reflective optical window 442 toward the second optical pathway. Another portion of the scattering beam 492 may pass through the partially reflective optical window 442 and continue traveling through the third optical pathway 427 to be detected by the second optical detector 438, which may function as a reference detector.

Portions of the excitation beam 490 and the scattering beam 492 traveling through the second optical pathway 436 in the example of FIG. 4 encounter partially reflective optical window 444. A portion of the excitation beam 490 and the scattering beam 492 encountering the partially reflective optical window 444 may be reflected by the partially reflective optical window into the first optical pathway optical pathway 426. These beams reflected into the first optical pathway 426 are directed to the fluid sample under analysis via an optical lens 428 disposed between the first optical pathway and the fluid sample. In some examples, another portion of the excitation beam 490 and the scattering beam 492 encountering the partially reflective optical window 444 may pass through the partially reflective optical window into the beam dump 446. The beam dump 446 may be an optically absorbent region of optical sensor 402 positioned on an opposite side of the first optical pathway 426 from the second optical pathway 427. The beam dump may absorb light directed into the region, e.g., to help prevent the light from reflecting back into first optical pathway 426 and being detected by optical detector 434.

As previously described, the excitation beam 490 traveling into the fluid sample via optical lens 428 may excite fluorescence in the sample while the scattering beam 492 traveling into the fluid sample may scatter, e.g., by suspended materials in the sample such as oil or particulates. In some examples, the fluorescent light emitted by the fluid sample in response to the excitation beam 490 is at a third wavelength different from the wavelength or wavelengths encompassed by either the excitation beam 490 or the scattering beam 429. Depending on the fluid sample under analysis, the third wavelength may be in the UV or near-UV spectrum, such as in a range from approximately 285 nm to approximately 385 nm (e.g., a wavelength greater than 300 nm, such as 315 nm). Fluoresced light and scattered light can be captured by the optical lens 428 and directed back into the first optical pathway 426 of the sensor 402. In some embodiments, the optical lens 428 acts to substantially collimate the fluoresced and scattered light into an emission beam 494 and a scattered beam 496, respectively, which travel back through the optical pathway 426 toward the partially reflective optical window 444.

In the configuration of FIG. 4, the partially reflective optical window 444 may transmit at least a portion of the emission beam 494 generated by fluorescing molecules in the fluid sample under analysis and also at least a portion of the scattered beam 496 generated by light scattering caused by the fluid sample. The emission beam 494 and scattered beam 496 may enter optical sensor 402 via optical lens 428 and travel through the first optical pathway 426 before encountering partially reflective optical window 444. Upon impinging upon the partially reflective optical window 444, at least a portion of the emission beam 494 and scattered beam 496 may pass through the partially reflective optical window and be detected by optical detector 434.

In some embodiments, the partially reflective optical window 444 may transmit more light or wavelengths of light to the first optical detector 434 than is desired to optically characterize the fluid sample under analysis. For example, the partially reflective optical window 444 may allow some portion of the excitation beam 490 to pass therethrough, such that scattering of the excitation beam 490 off the fluid sample may reach the first optical detector 434 and be detected as corresponding to fluorescent emissions emitted by the fluid sample. To help control the light received and detected by the optical detector 434, the optical sensor 402 may include an optical filter 432 disposed between the optical lens 428 and the first optical detector 434 to filter out undesired light. In the embodiment of FIG. 4, the optical filter 432 is positioned between the partially reflective optical window 444 and the first optical detector 434. In some embodiments, the optical filter 432 is designed to filter out substantially all wavelengths of light (and, in other examples, all wavelengths of light) emitted by the first optical emitter 420. This may help prevent light emitted by the first optical emitter 420 that does not generate fluorescent emissions from being detected by the optical detector 434 and characterized as fluorescent emissions (e.g., light from the first optical emitter 420 that travels toward the optical detector 434 rather than toward optical lens 428 and/or light from the optical emitter that scatters in the fluid sample rather than generates fluorescent emissions). The optical filter 432 may transmit substantially all (and, in other examples, all) wavelengths of fluorescent emissions emitted from the fluid sample in response to the light from the first optical emitter 420 and wavelengths of light scattered by the fluid sample in response to light from the second optical emitter 424.

The first optical detector 434 can be configured to detect or measure the intensity and/or other properties of incident light thereupon. As described, the first optical detector 434 may receive at least a portion of the scattered beam 496 and the emission beam 494 transmitted from the fluid sample through the partially reflective optical window 444. In some embodiments, such as that shown in FIG. 3, the first optical detector 434 can comprise a single detector configured to detect light from both the emission beam 494 and the scattered beam 496. In such an arrangement, optical sensor 402 may control the first optical emitter 420 and the second optical emitter 424 to alternatingly emit the excitation beam 490 and the scattering beam 492. Light detected by the optical detector 434 in response to light emitted by the first optical emitter 420 (e.g., when the second optical emitter 424 is not emitting light) can be attributed to fluorescent emissions generated in the fluid sample. Conversely, light detected by the optical detector 434 in response to light emitted by the second optical emitter 424 (e.g., when the first optical emitter 420 is not emitting light) can be attributed to light scattering caused by the fluid sample. In this way, a single detector can detect and resolve both the emission beam 494 and the scattered beam 496 emanating from the fluid sample under analysis.

As previously described, the first optical detector can detect light fluoresced from the fluid sample and received as at least one emission beam 494. In some embodiments, the intensity of the emission beam 494 can be measured to calculate a characteristic of the sample, for example the concentration of a fluorophore. In one example, the fluoresced light from the sample is measured while light from the first optical emitter 420 is emitting and incident on the fluid sample. In another example, the fluoresced light from the sample is received and measured after light from the first optical emitter 420 ceases emitting. In these examples, fluorescence emitted by the fluid sample may persist beyond the duration of emission from the first optical emitter 420. Accordingly, the first optical detector 434 may receive fluorescent emissions from the fluid sample subsequent to ceasing emission of light from the first optical emitter 420. In some examples, optical sensor 402 may determine a characteristic of the fluid sample under analysis based the magnitude of fluorescent emissions detected by the first optical detector 434 and the change in that magnitude over time after ceasing light emission by the first optical emitter 420. For example, the optical sensor 402 may perform time-resolved fluorescence spectroscopy by measuring a fluorescence decay curve (e.g., fluorescence intensity as a function of time) for the fluid sample. This may involve measuring fluorescent emissions emanation from the fluid sample under analysis from a time when the first optical emitter 420 ceases emitting light to a time when the first optical detector 434 ceases detecting fluorescent emissions from the fluid. In addition to detecting fluorescent emissions, light scattered off the fluid sample and returned to the sensor in the form of a scattered beam 496 can also be detected by optical detector 434.

In some examples, the amount of fluorescence emitted by the fluid sample under analysis is dependent upon the amount of excitation light directed into the sample by the first optical emitter 420. Likewise, the amount of light scattered by the fluid sample may be dependent upon the amount of scattering light directed into the sample by the second optical emitter 424. In such examples, the intensity of light emitted by the first optical emitter 420 and/or the second optical emitter 424 can be measured, e.g., by second optical detector 438. Optical sensor 402 can then adjust the magnitude of the fluorescent emissions and/or scattered light detected by the first optical detector 434 based on the magnitude of light emitted by the first optical emitter 420 and/or the second optical emitter 424.

An optical sensor in accordance with the disclosure can be used as part of a system (e.g., fluid system 100 in FIG. 1) in which the sensor is communicatively coupled to a controller to receive data from and send data to the sensor. The controller may include an integral component such as a microcontroller, or an external component, such as a computer. The controller can be in communication with the first and second optical emitters, as well as the first and second optical detectors. The controller can be configured to control the first and second optical emitters to emit light at a first wavelength and a second wavelength, respectively. As discussed, the first wavelength may excite fluorescence in a fluid sample, while the second wavelength may scatter off of the fluid sample. The controller can also be configured to control the first optical detector to detect fluorescent emissions emitted by the fluid sample and also light scattered by the sample. The controller can be further configured to determine at least one characteristic of the fluid sample based on the detected fluorescent emissions. For example, the controller may determine a characteristic of the fluid sample based data generated by the optical sensor and information stored in a memory associated with the controller, such as calculating based on an equation, finding in a lookup table, or any other method known in the art.

In applications where the first and second optical emitters are operated in an alternating sequence of activation, the controller can coordinate the frequency and duration of light emissions from each optical emitter. In addition, in embodiments where the sensor includes a second optical detector that functions as a reference detector, the controller can detect light from the first and second optical emitters and use this detected light to calibrate light detected by the first optical detector.

In some examples, an optical sensor according to the disclosure also includes one or more non-optical sensors. Exemplary non-optical sensors can include, but are not limited to, pH sensors, conductivity sensors, and temperature sensors. Data from the non-optical sensors can be used determine non-optical characteristics of the sample under analysis. In some embodiments, data from one or more non-optical sensors can be used to adjust a measurement of fluorescent emissions from a fluid sample to determine one or more characteristics of the sample. For example, a temperature sensor can be mounted in a sensor body to correct for temperature effects on fluorescence as well as on electronics and/or detectors. In other examples, data from a non-optical sensor may be used to monitor a fluid sample and/or control a fluid process in addition to or in lieu of using optical sensor data to monitor the fluid sample and/or control the fluid process.

As discussed, in certain embodiments, an optical sensor according to the disclosure may detect light fluoresced from a sample at one or more wavelengths and scattered off of the sample at yet another wavelength. The optical sensor may also detect additional characteristics, such as non-optical characteristics, of the fluid sample. Data generated by the optical sensor can be used to calculate or otherwise determine at least one characteristic of the sample. Such data can be received simultaneously, alternatingly in sequence, or in a combination in which some but not all data can be received simultaneously.

The received data contributing to determining at least one characteristic can be received in a plurality of channels. Channels can be optical channels, comprising one or more fluorescence channels and a scattering channel, but can also include data channels such as data received from one or more non-optical sensors. Optical channels can be defined by wavelength bands, for example. Accordingly, in some embodiments, data is received in the form of a first fluoresced wavelength is data received in the first fluorescent channel, while data received in the form of light scattered off the sample is data received in the scattering channel. Thus, in various embodiments, the optical sensor can receive data in any combination of optical channels via the first optical pathway simultaneously and/or alternatingly, and additionally in non-optical channels from one or more non-optical sensors. In addition, as previously described, the second optical detector can receive light from the first and second optical emitters used for calibration of measurements at the first optical detector. Thus, the data received at the second optical detector can be received in one or more calibration channels.

In applications where the optical sensor includes a single optical detector that detects fluorescent emissions received from the fluid sample and also detects scattered light received from the fluid sample, the first and second optical emitters may activate and deactivate in alternating sequence. This may allow data generated by the optical detector to be resolved into fluorescent emission data corresponding to detected fluorescent emissions and scattering data corresponding to detected scattered light. In other examples, the optical sensor can include multiple optical detectors that detect fluorescent emissions received from the fluid sample and detect scattered light received from the fluid sample. For example, the optical sensor may include one optical detector that detects fluorescent emissions received from the fluid sample and another optical detector that detects scattered light received from the fluid sample.

Figure 5A:
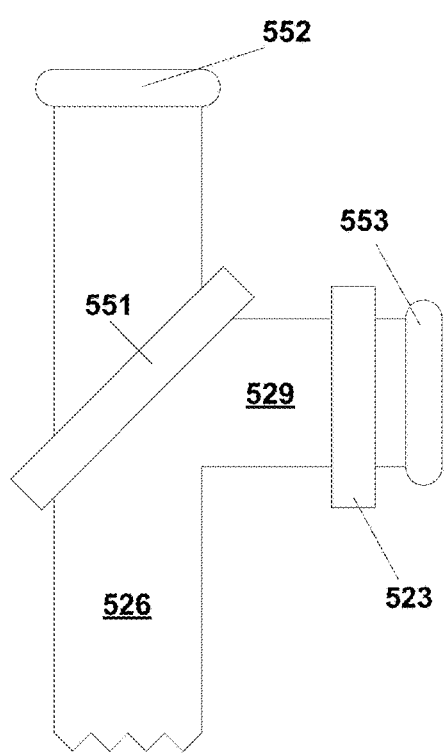
FIGS. 5A and 5B illustrate example optical detector arrangements that may be used in the optical sensor of FIG. 2.
Figure 5B:
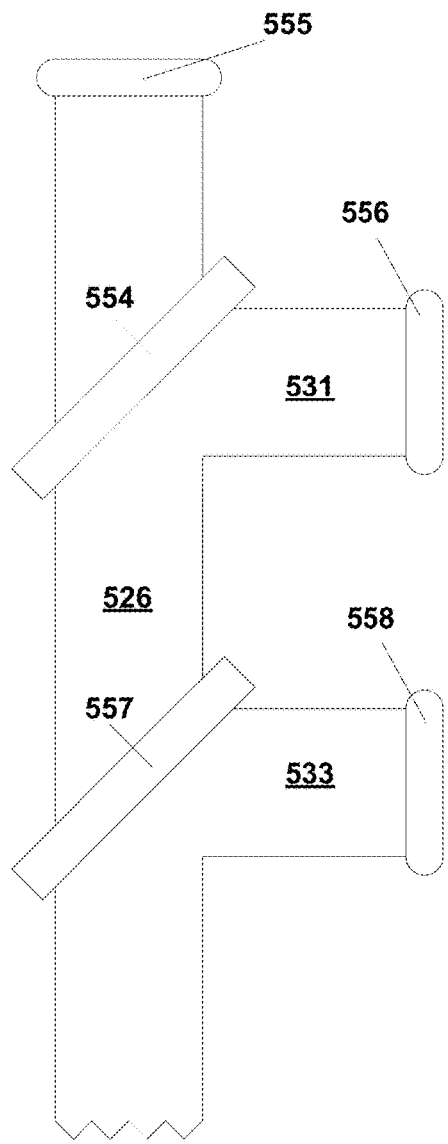

FIGS. 5A and 5B illustrate example alternative optical detector arrangements that can be used in an optical sensor, such as the optical sensors of FIGS. 2-4. FIG. 5A illustrates an exemplary embodiment in which an optical detector (e.g., optical detector 334 and/or optical detector 338 in FIG. 3) includes a first optical detector element 552 and second optical detector element 553. According to some embodiments, the sensor can comprise at least one additional optical pathway, such as a fourth optical pathway 529 intersecting the first optical pathway 526, e.g., at an approximately 90 degree angle. In conjunction with FIG. 3, at least one additional optical pathway is disposed between a partially reflective optical window 551 and a terminal end of the first optical pathway 526 opposite the lens.

In some embodiments, the sensor can comprise at least one additional partially reflective optical window 551 positioned at the intersection of the first optical pathway 526 and a corresponding additional optical pathway, such as the fourth optical pathway 529. The additional partially reflective optical window 551 is configured to reflect or transmit a select band of light toward a corresponding optical detector element. For example, FIG. 5A shows an additional partially reflective optical window 551 disposed at intersection of the first optical pathway 526 and the fourth optical pathway 529. First 552 and second 553 optical detector elements are located at terminal ends of the first 526 and fourth 529 optical pathways, respectively.

In some embodiments, the partially reflective optical window 551 is configured to transmit light at wavelength "A" and reflect light at wavelength "B". Thus, if a mixture of light of wavelengths "A" and "B" travel through the first optical pathway 526 from the sample toward the partially reflective optical window 551, the partially reflective optical window 551 will act to reflect the light of wavelength "B" to the second optical detector element 553 while transmitting the light of wavelength "A" to the first detector element 552. This allows each detector element to detect light at a different wavelength or range of wavelengths, and allows for the sensor to implement optical detector elements that can detect a narrow band of wavelengths. In this example, the partially reflective optical window 551 directs light, such as an emission beam and a scattered beam, to two corresponding optical detector elements simultaneously.

In some embodiments, the first additional partially reflective optical window 551 is configured to direct light fluoresced from the sample toward the second optical detector element 553 while directing light scattered off the sample at, for example, the second wavelength, toward the first optical detector element 552. In such an embodiment, scattered light and fluoresced light can be measured simultaneously, since each is measured by a different detector element.

As described previously with respect to FIG. 3, there may be situations in which light of an undesired wavelength is directed toward a particular detector element, which can introduce errors into the measurement of the detected light. Thus, an additional optical filter can be placed between the partially reflective optical window 551 and a corresponding detector element. For example, an additional optical filter 523 can be placed between additional partially reflective optical window 551 and the second detector element 553 in FIG. 5A. When used, the optical sensor can have as many additional filter elements as necessary. In some embodiments, the sensor includes at least as many filter elements as optical detector elements.

FIG. 5B illustrates an exemplary embodiment similar to FIG. 5A in which an optical detector (e.g., optical detector 334 and/or optical detector 338 in FIG. 3) includes multiple optical detector elements. In particular, FIG. 5B illustrates an optical detector arrangement that includes a first optical detector element 555, a second optical detector element 556, a third optical detector element 558, a fourth optical pathway 531, and a fifth optical pathway 533. The fourth and fifth optical pathways intersect the first optical pathway 526, e.g., at an approximately 90 degree angle. In addition, in this example, the optical detector arrangement includes partially reflective optical windows 554 and 557 to control light flow from the first optical pathway 526 to the fourth and fifth optical pathways, respectively.

In the illustrated embodiment, the partially reflective optical window 557 is located at the intersection of the first 526 and fifth 533 optical pathways. The second additional partially reflective optical window 557 can be configured to selectively transmit or reflect particular wavelength or band of wavelengths, thereby directing only a certain band of wavelengths toward the third detector element 558. In some configurations, the sample under analysis can fluoresce at a plurality of wavelengths, for example, encompassing first and second fluorescent wavelengths and forming first and second emission beams, respectively. In such a case, the partially reflective optical window 557 can reflect the second emission beam toward the third optical detector element 558, while allowing the first emission beam and, for example, a scattered beam to pass therethrough. Subsequently, the partially reflective optical window 554 can reflect the first emission beam toward the second optical detector element 556 while allowing the scattered beam to pass therethrough toward the first optical detector element 555. Such an embodiment can be utilized, for example, to detect light in three distinct channels simultaneously—a first fluorescent channel, a second fluorescent channel, and a scattering channel.

It will be appreciated that, while described as possible variations of a first optical detector such as that shown in FIG. 3, the embodiments shown in FIGS. 5A and 5B can also be used for a second optical detector (e.g., reference detector as well). In such configurations, the partially reflective optical windows may be configured to selectively reflect or transmit first and second wavelengths emitted by the first and second optical emitters, respectively. For example, with reference back to FIG. 3, a detector such as that shown in FIG. 5A can be used to direct the scattering beam toward the first optical detector element 552 and the excitation beam toward the second optical detector element 553, separating and enabling simultaneous detecting of calibration channels.

An optical sensor according to the disclosure can be modified to meet requirements for use in specific applications or configurations. For example, FIGS. 6A-6D illustrate a sensor attached to various components for use with a fluid vessel. FIGS. 6A-6D also illustrate different sensor components and physical arrangements that can be used by any sensor according to the disclosure.

Figure 6A:
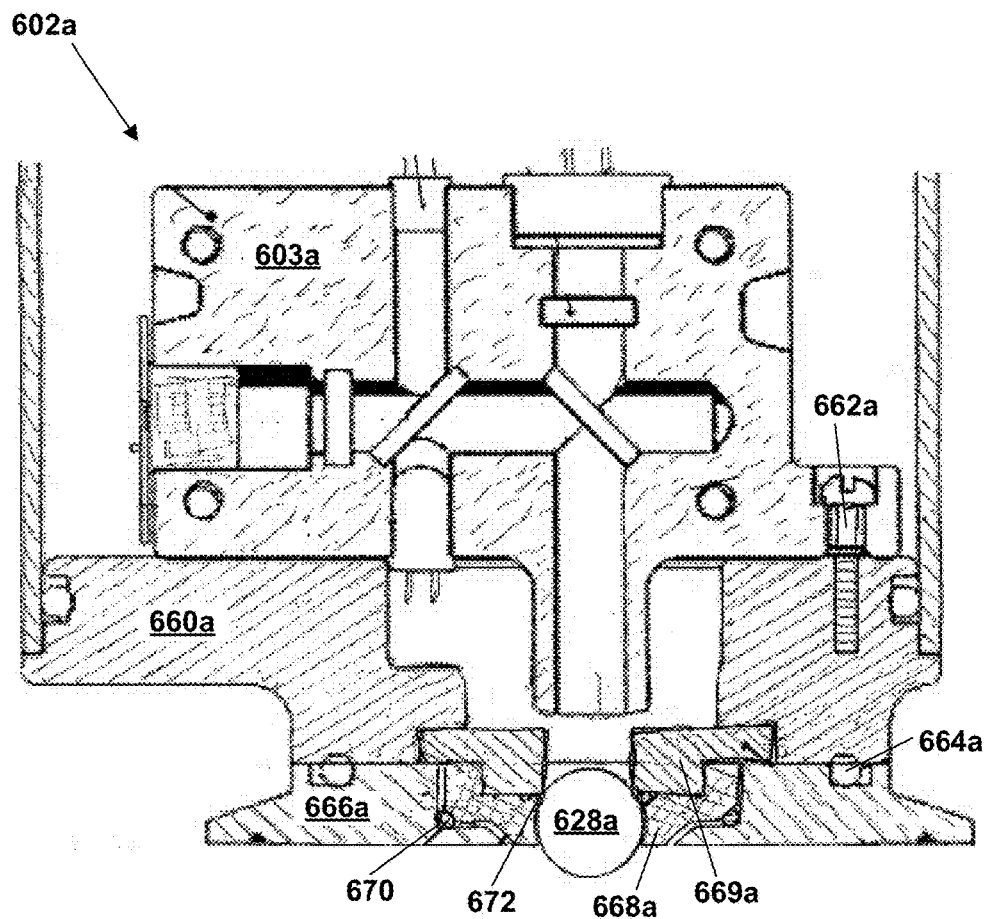
FIGS. 6A-6D illustrate example optical sensor housing and component arrangements that may be used for the optical sensor of FIG. 2.

As shown in FIG. 6A, the housing 603a of a sensor 602 (which may be a sensor such as that shown and described with respect to FIG. 3) can be secured to a mounting disc 660a via one or more attachment members such as a screw 662a. The mounting disc 660a shown in FIG. 6A is attached to a cover 666a with screws (not shown), for example, and sealed thereto via an O-ring 664a. The cover 666a can be made of any appropriate material for the desired application of the sensor 602, such as stainless steel, plastic, or the like. In some embodiments, the cover 666a comprises a standard stainless steel solid end cap which is regularly used for sanitary fittings. In some embodiments, the cover 666a engages an insert 668a, which can be selected from a set of interchangeable inserts. The insert 668a can be made of any appropriate material for the desired application of the sensor 602, and can be configured to hold the lens 628a for emitting light to and receiving light from the sample. The insert 668a can be secured in the cover 666a with a washer 669a. O-rings 670, 672 can create seals at the interface of the cover 666a and insert 668a, and insert 668a and lens 628a, respectively.

In some embodiments, the insert 668a can be made of plastic, for example a polysulfone or a fluoropolymer. In other embodiments, the insert 668a can be made of polyphenylene sulfide or 40% glass filled polyphenylene sulfide. The insert 668a can have an external diameter larger than an internal diameter of a counterbore in the cover 666a, allowing the insert 668a to be press-fit into the cover 666a without the need for O-ring 670. In some embodiments, the lens 628a can comprise a sapphire ball and the insert can comprise an internal hole, relatively sized such that the internal hole in the insert 668a can have a diameter smaller than the diameter of the sapphire ball. In such cases, the lens 628a can be press-fit into the insert 668a, providing a hermetic seal without the need for O-ring 672. In such a case, one possible combination of materials for sensor parts to be immersed in a fluid sample comprises stainless steel for the cover 666a, 40% glass filled polyphenylene sulfide for the insert 668a and sapphire for the lens 628a.

It will be appreciated that tolerances for the cover, the insert, and the lens can be selected to provide hermetic seals at their interfaces without requiring O-rings. The press-fit assembly of these parts immersed in the sample can be used, for example, within a temperature range of 0° C. to 90° C. and for pressures up to 150 psi. For high pressure applications, a washer 669a can be included to provide stable mechanical support for the insert 668a and the lens 628a. In some embodiments, the washer 669a does not contact the sample, and can be made of appropriate materials providing the necessary strength for supporting the insert 668a and the lens 628a in high pressure applications such as stainless steel, plastic and the like.

Figure 6B:
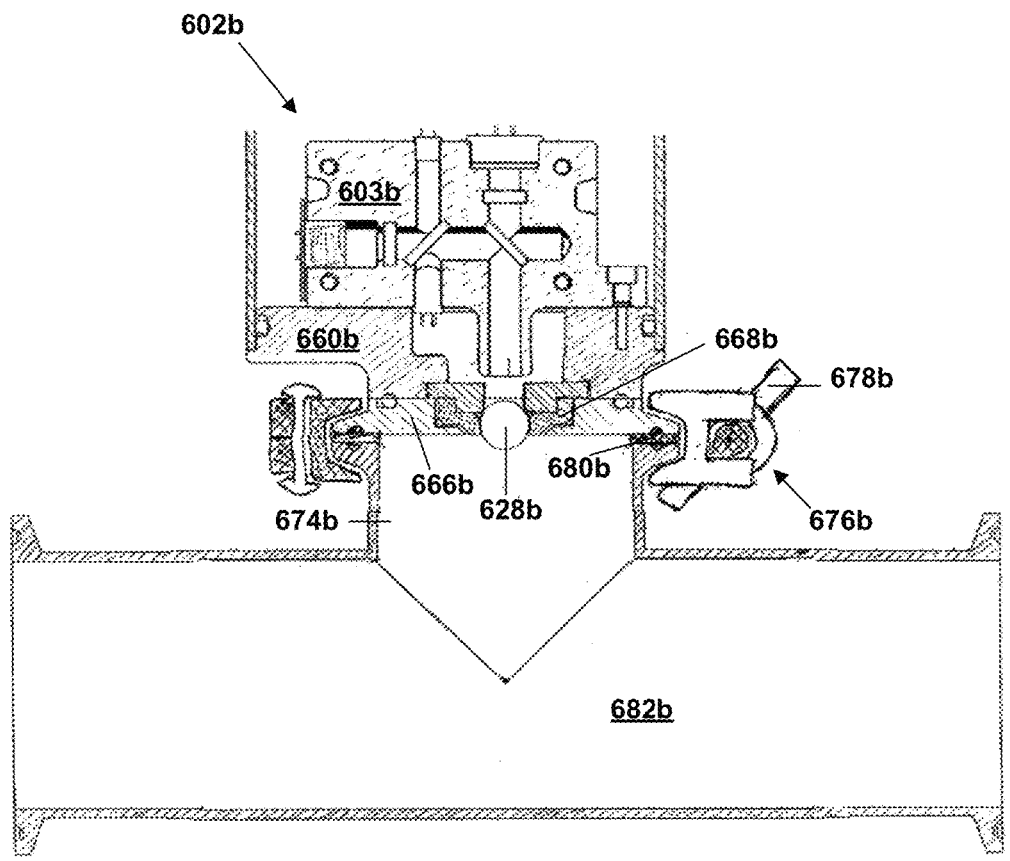

FIG. 6B shows a sensor 602b assembly in which the housing 603b is secured to a mounting disc 660b, comprising a cover 666b engaging an insert 668b holding a lens 628b. The sensor 602b assembly is secured to a short tee segment 674b by a clamp 676b comprising a nut 678b. An O-ring gasket 680b can be positioned between the assembly and the tee 674b to create a seal between the interior of the sensor/fluid sample and the external environment. In an exemplary embodiment, the sensor 602b is secured to a flange on a fluid vessel 682b via a clamp, though any device for securing the sensor 602b to the vessel 682b can be used. A fluid vessel can comprise any structure to support or house the fluid to be analyzed, including a static fluid reservoir, a tank, a pipe, or any other fluid handling structure, including fluid handling structures that accommodate flowing and non-flowing volumes of fluid.

A configuration such as that shown in FIG. 6B can be used in, for example, a CIP system in which a cleaning or sanitation process occurs in the vessel and the sensor determines a characteristic of a solution used in the process. The vessel 682b can comprise, for example, a food product tank, a chemical storage tank, a membrane assembly, a pipe line, or other CIP equipment. The lens 628b in the configuration shown in FIG. 6B is positioned proximate a distal end of the housing extending toward the vessel 682b.

Figure 6C:
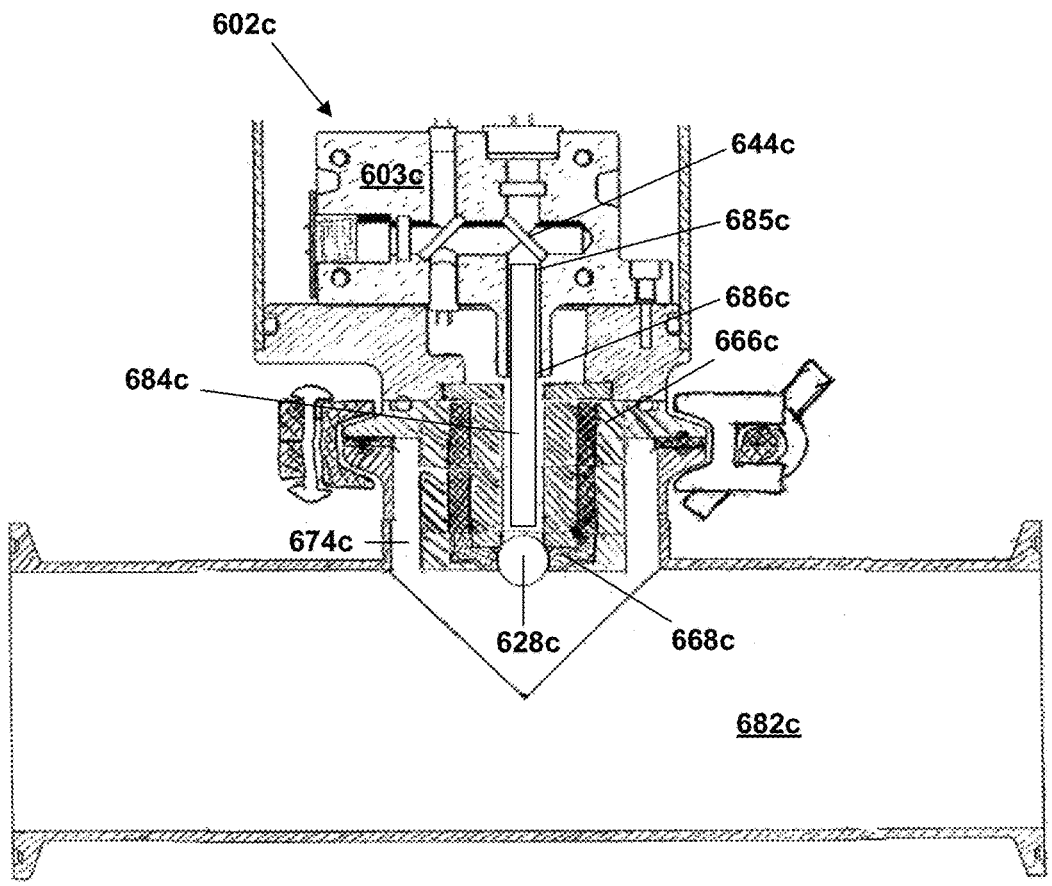

FIG. 6C shows a sensor 602c assembly similar to that of FIG. 6B where the assembly is secured to a tee segment 674c, however in this embodiment, the insert 668c engaging the cover 666c is configured to hold the lens further from the distal end of the housing, nearer the sample in the vessel 682c. Insert 668c can be changeably secured to the cover 666c and/or the sensor 602c, as well as to the lens 628c, allowing for interchangeability of the location of the lens 628c relative to the housing 603c as well as to the sample in the vessel 682c. For example, in some embodiments, only the insert 668c and a press-fit lens 628c protrude into the sample vessel 682c. Alternatively, the cover 666c can comprise a metal (e.g., stainless steel) cylinder and a flange, and can extend into the sample vessel 682c while providing mechanical support and protection for the insert 668c and the lens 628c.

In addition, FIG. 6C illustrates sensor 602c as including a light guide 684c. Light guide 684c is inserted within the optical pathway between ball lens 628c and partially reflective optical window 644*c*. The light guide 684*c* may be a structure that guides light from the ball lens 628*c* to the partially reflective optical window 644*c*. Any suitable light guide can be used and, in one example, light guide 684*c* is made from a solid rod of optically transparent material (e.g., quartz) with polished ends. When used, the diameter of the light guide 684*c* may be smaller than the inner diameter of the optical pathway extending between the ball lens 628*c* and the partially reflective optical window 644*c*, and can be aligned and secured in such a way so as to limit light losses.

To hold the light guide 684*c* within the optical pathway of optical sensor 602*c*, the light guide may be friction fit within the optical pathway, mechanically affixed within the optical pathway, or otherwise secured within the housing. For example, FIG. 6C illustrates the optical sensor housing as having two narrow areas 685*c* and 686*c* each having a smaller diameter than the diameter of the light guide 684*c* and providing a press fit for the light guide. With such mounting, the light guide 684*c* may have unobstructed ends that allow the light guide to receive and emit light across substantially its entire cross-section. In some embodiments, substantially all of the external surfaces of the light guide are surrounded by air, creating a condition for total internal reflection and channeling light through the light guide 684*c*. By using the light guide 684*c*, the electrical and optical components of sensor 602*c* may be positioned farther from the vessel 682*c* than if the light guide was not used while still generating acceptable signal strength. This may help keep temperature sensitive components (e.g., LEDs, photodiodes) at a farther distance from hot fluid within the vessel.

Figure 6D:
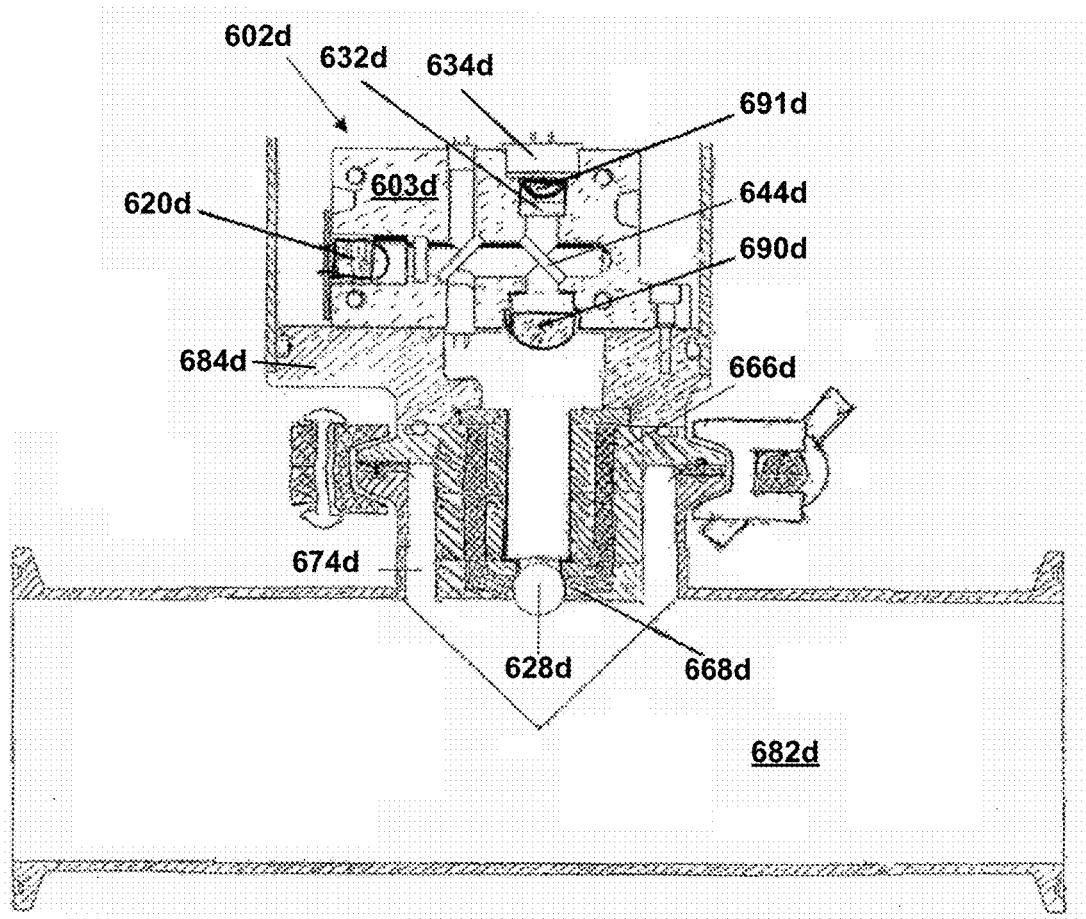

FIG. 6D shows a sensor 602*d* assembly similar to that of FIGS. 6B and 6C where the assembly is secured to a tee segment 674*d*. In the example of FIG. 6D, however, the sensor 602*d* also includes a collimating lens 690*d* positioned within the optical pathway between the ball lens 628*d* and the partially reflective optical window 644*d*. The collimating lens 690*d* is illustrated as being positioned adjacent the partially reflective optical window 644*d* (e.g., closer to the partially reflective optical window than the ball lens 628*d*). In operation, the collimating lens 690*d* can collect light from the optical emitter 620*d* and direct the light on the ball lens 628*d*, thereby creating focused excitation within fluid in close proximity to the ball lens. In addition, the collimating lens 690*d* can collect light received from the ball lens 628*d* (e.g., fluorescence) and direct the light on optical detector 634*d*. Although the size of the collimating lens 690*d* will vary when used, for example based on the size of the optical sensor, in some examples, the collimating lens has a diameter ranging from approximately 12 millimeters (mm) to approximately 20 mm.

By using the collimating lens 690*d*, the magnitude of the optical signal detected by optical detector 634*d*, and hence the strength of the electrical signal generated by the optical detector, may increase as compared to if the optical sensor does not include the collimating lens. For example, adding the collimating lens 690*d* adjacent the partially reflective optical window 644*d* may increase the magnitude of excitation received through the ball lens 628*d* by a factor greater than two (e.g., a range from two to three times what would otherwise be received). The total increase in fluorescent signal strength detected by the optical detector 634*d* may increase by a factor greater than five (e.g., a range from six to ten times what would otherwise be detected) when using the collimating lens 690*d* as compared to when the sensor does not include the collimating lens. In some examples, an additional focusing lens 691*d* may be placed between the emission filter 632*d* and the optical detector 634*d* to focus fluorescent light on a smaller area of the detector. This may allow the optical sensor 602*d* to use a smaller sensitive area photodiode with higher shunt resistance and lower terminal capacitance, providing higher stability in a wide range of temperatures.

Figure 7:
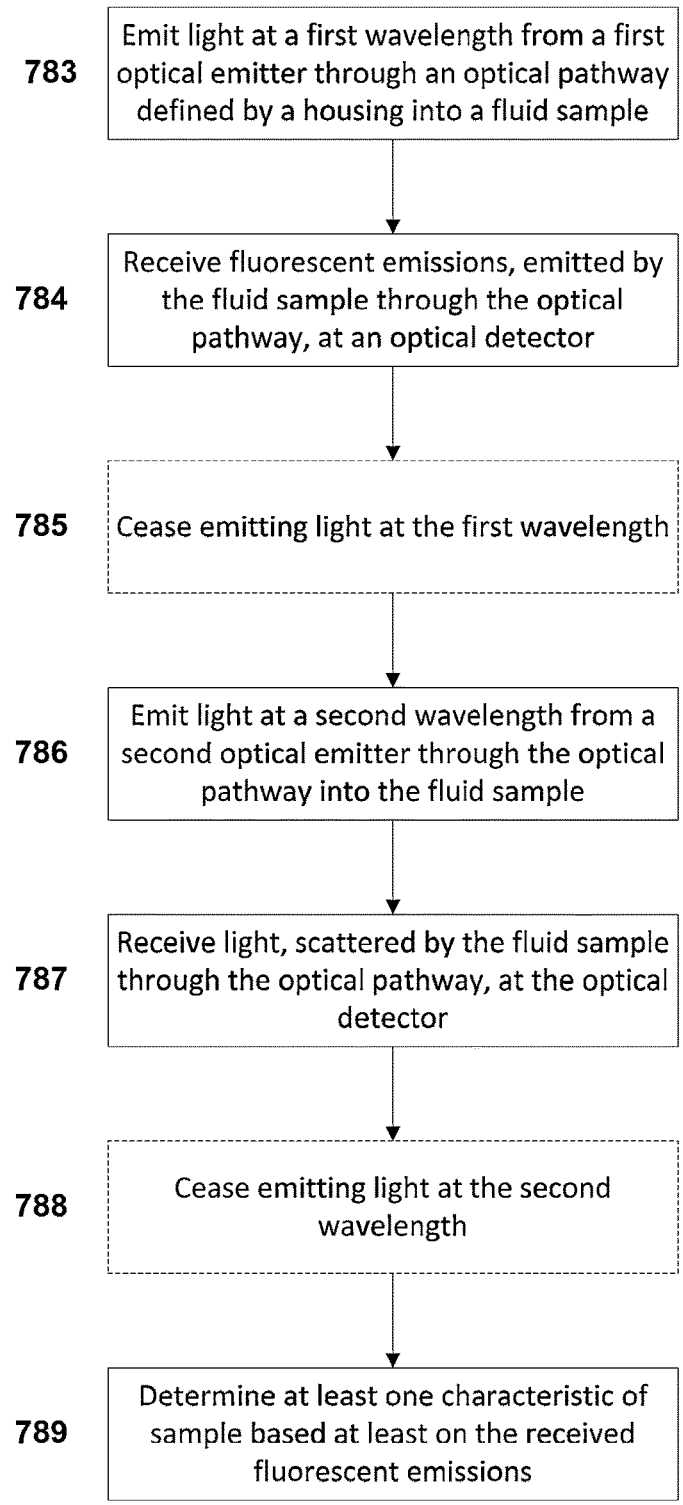
FIG. 7 is a process flow diagram illustrating exemplary operation of a sensor.

Various embodiments and configurations of sensors have been described. FIG. 7 is a process flow diagram of an optical analysis technique according to the disclosure. FIG. 7 illustrates a process in which a sensor emits light at a first wavelength 783 from a first optical emitter through an optical pathway and into a fluid sample. The optical pathway is defined by a housing of the sensor. The sensor also receives fluorescent emissions 784 emitted by the fluid sample through the optical pathway at an optical detector. In some embodiments, the fluorescent emissions are excited by the light emitted by the first optical emitter. The sensor emits light at a second wavelength 786 from a second optical emitter, through the optical pathway and into the fluid sample. The light of the second wavelength is directed to the sample via the same optical pathway as the first wavelength. The sensor also receives light, scattered by the fluid sample 787 through the optical pathway, at the optical detector.

In the process of FIG. 7, light is emitted at the first wavelength and second wavelength into a fluid sample, as well as received from the fluid sample, via a single optical pathway. Received light can be scattered off the sample, and in some embodiments, comprises light of the second wavelength scattered off the sample. Received light can also be in the form of light fluoresced from the sample, which can be caused by the light of the first wavelengths. As discussed previously, in some embodiments, the sensor is unable to resolve the difference in light scattered by the sample and fluoresced from the sample if they are simultaneously incident on the optical detector. Thus, in some embodiments, emitting light at the first wavelength is ceased 785 prior to emitting light at the second wavelength 786. For the same reason, should the process be repeated, in some embodiments, emitting light at the second wavelength is ceased 788 prior to emitting light at the first wavelength 783. The steps of ceasing emitting light at the first and second wavelengths are shown in broken lines to illustrate that such steps can be taken, but need not be in every embodiment.

In further embodiments, emitting light at the first wavelength is ceased 785 prior to receiving useful fluorescent emissions at the optical detector. This can be done, for example, if a sample contains multiple fluorescing species that fluoresce for different durations, such that the fluorescence from one species persists longer than that from another species. If fluorescence from the longer persisting species is desired to be measured while fluorescence from the shorter persisting species is extraneous, it can be advantageous to cease emitting light at the first wavelength, wait for the fluorescence excited by the shoring persisting species to subside, and then measure the remaining fluorescent emissions attributable to the longer persisting species. It should be noted that the optical detector may be receiving fluorescent emissions from the sample while light of the first wavelength is being emitted; however, the measurement of fluoresced light may or may not be disregarded until the appropriate time.

Finally, in the example of FIG. 7, the process can include the step 789 of determining at least one characteristic of the sample based on the received fluorescent emissions. For example, as discussed previously, the fluorophore concentration of the sample can be determined based on the received fluorescence from the sample.

It will be appreciated that the process outlined in FIG. 7 can be performed by a controller in a system comprising a sensor. The controller can include a processor for controlling the timing and duration of emitting light from either the first or second optical emitters, as well as the timing of receiving light from the fluid sample. That is, the controller can be programmed to disregard received light when there is extraneous light present that can disrupt the ability to adequately determine the at least one characteristic of the sample. The controller can utilize data from received fluoresced light, scattered light, and any other data that it receives to calculate or otherwise determine, or adjust the determination of, at least one characteristic of the sample.

Exemplary sensors have been described. Some embodiments comprise multi-channel fluorometric sensors in which fluorescence from a sample is excited and detected in at least one fluorescence channel, and the detected fluorescence is used to determine a characteristic of the sample. Other factors, such as light scattered off the sample, or additional non-optical measurements can be used to supplement the fluorescence detection and account for potential variations in fluorescence of the sample. The sensor can be part of a system comprising a controller to automate the control of emitters and detectors, and calculate or otherwise determine characteristics of the sample from measured data. Sensors can be secured into vessels in which fluid samples to be characterized are present or flow through.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "controller" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a non-transitory computer-readable medium, such as a computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

The following example may provide additional details about an optical sensor in a system used to determine concentrations of components within a fluid sample.

EXAMPLE

An example optical sensor was constructed in accordance with the disclosure and then used to optically analyze a variety of samples having different concentrations of water and an aromatic fluorophore (AF). In addition to using the optical sensor to analyze the samples of water and AF, the components of the optical sensor were individually evaluated to optically characterize the components of the sensor.

Figure 8A:
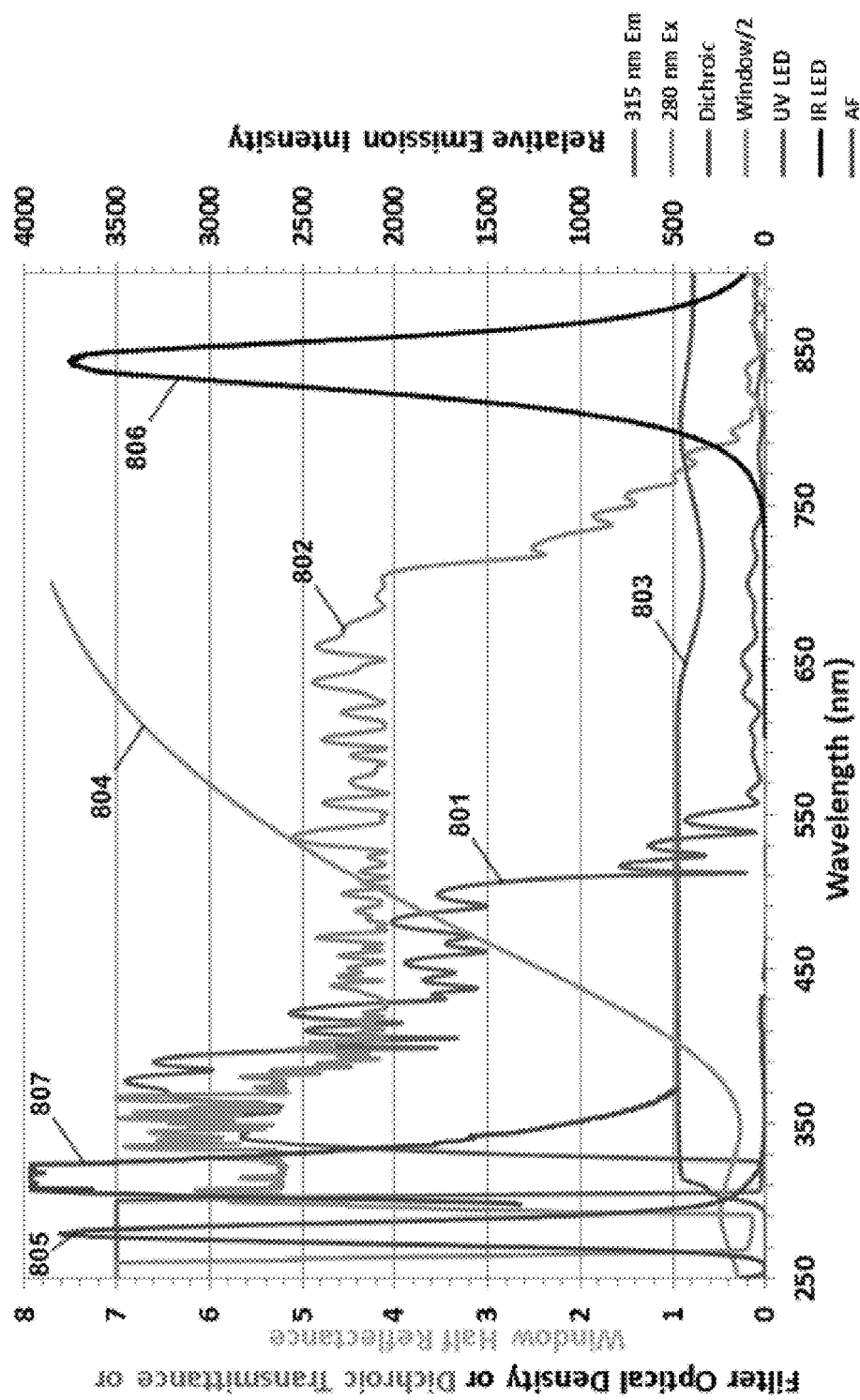
FIGS. 8A-8E are plots illustrating example optical data for an example sensor constructed in accordance with the disclosure.

FIG. 8A is a plot of several characteristics of the optical sensor, including dichroic transmittance 803, window half-reflectance 804 and filter optical density 801, 802 (along the left-hand y-axis) as a function of wavelength in nanometers (nm). Dichroic transmittance 803 is a characteristic of a dichroic filter (for example, 344 in FIG. 3) whose transmittance varies with wavelength. As shown in FIG. 8A, the measured dichroic transmittance 803 of the optical sensor was near zero at wavelengths significantly below 300 nm and approached one as the wavelengths approached about 320 nm. This characteristic makes the dichroic filter reflect UV light to the sample while transmitting fluorescence to detector (for example, 334 in FIG. 3). The measured window half-reflectance 804 represents half of the reflectance of a quartz window (for example, 342 in FIG. 3) as a function of wavelength. Incident light reflects much more strongly as the wavelength increases from about 350 nm to the near-IR range. This property of the quartz window allows high transmittance of the UV light while reflecting the IR light to the sample. Emission intensities of UV 805 and IR 806 LED's (for example, 320 and 324, respectively in FIG. 3) were measured as a function of wavelength and are shown. The optical filter densities of emission 801 and excitation 802 filters were measured as a function of wavelength and are plotted. The AF emission intensity 807 was also measured as a function of wavelength and is shown in the plot of FIG. 8A. As can be seen, the peak AF emission intensity 807 approximately corresponded to a minimum in the emission filter optical density 801, while the peak UV LED emission intensity 805 approximately corresponded to a minimum in the excitation filter optical density 802.

The plot in FIG. 8A also includes the emission intensity of an excitation UV LED 805 and fluoresced light from the AF in the sample 807 as a function of wavelength. In the characterized system, the excitation UV LED 805 had peak intensity near a wavelength of about 280 nm, while the fluoresced light from the AF 807 had a peak wavelength of about 315 nm. It can be seen, then, from the data in FIG. 8A that the transmittance 803 of the dichroic filter at the wavelength emitted by the UV LED 805 was relatively low, reflecting light intended to excite fluorescence. However, the transmittance 803 was closer to one at the wavelengths of the excited fluorescence 807 and the IR light 806 scattered from the sample. These wavelengths are intended to be transmitted through the dichroic filter to the detector for analysis.

Figure 8B:
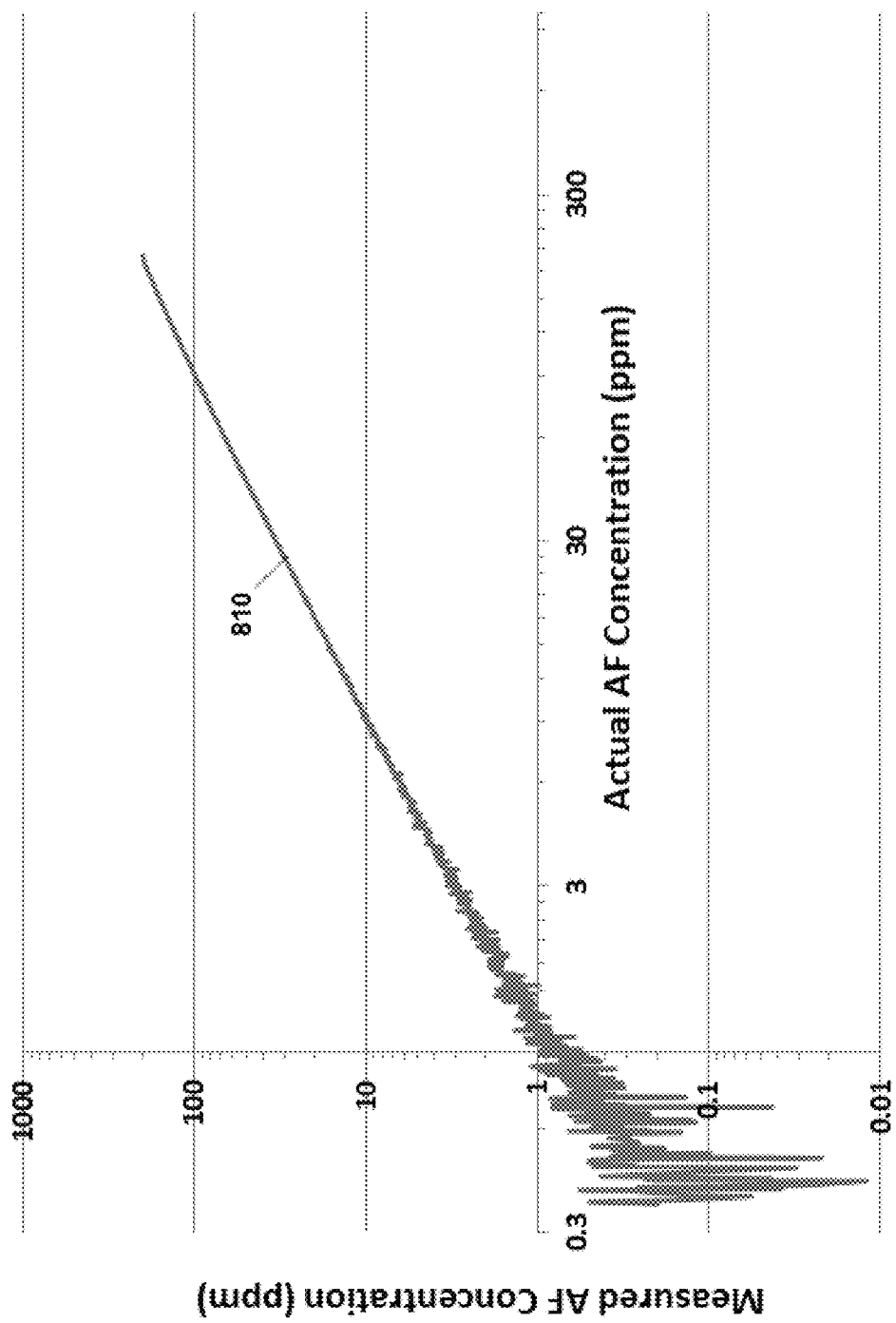

FIG. 8B is a plot comparing a measured AF concentration of the sample to the actual AF concentration, each in parts-per-million (ppm), at a variety of known concentrations. The concentration data 810 in FIG. 8B can be used to determine the AF concentration range in which the optical sensor yields relatively consistent and accurate results.

Figure 8C:
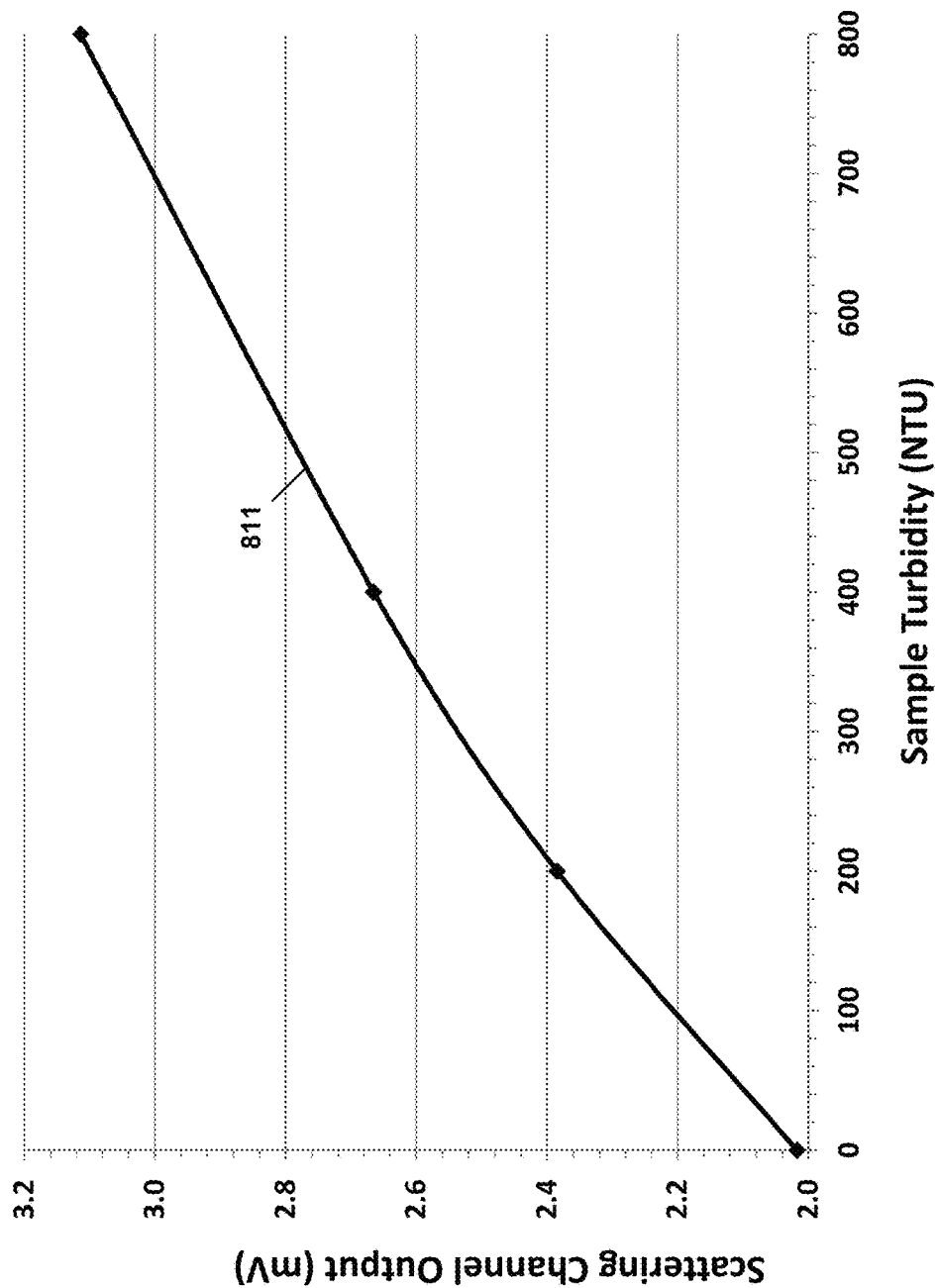

FIG. 8C is a plot of the detector output 811 in the scattering channel in millivolts (mV) as a function of the sample turbidity in nephelometric turbidity units (NTU). To generate the data of FIG. 8C, the optical sensor scattering beam was directed to a sample of water and milk (to promote scattering), causing light to scatter back into the sensor to be detected by a detector housed within the optical sensor. The detector received the scattered light and outputted a voltage 811 indicative of the measured intensity. The amount of light scattered by the sample depended on the turbidity of the sample and, as a result, can be used to determine the turbidity of the sample. The turbidity of the sample can affect the fluorescent properties of the sample and, consequently, can be taken into account when determining a concentration from a fluorescence measurement.

Figure 8D:
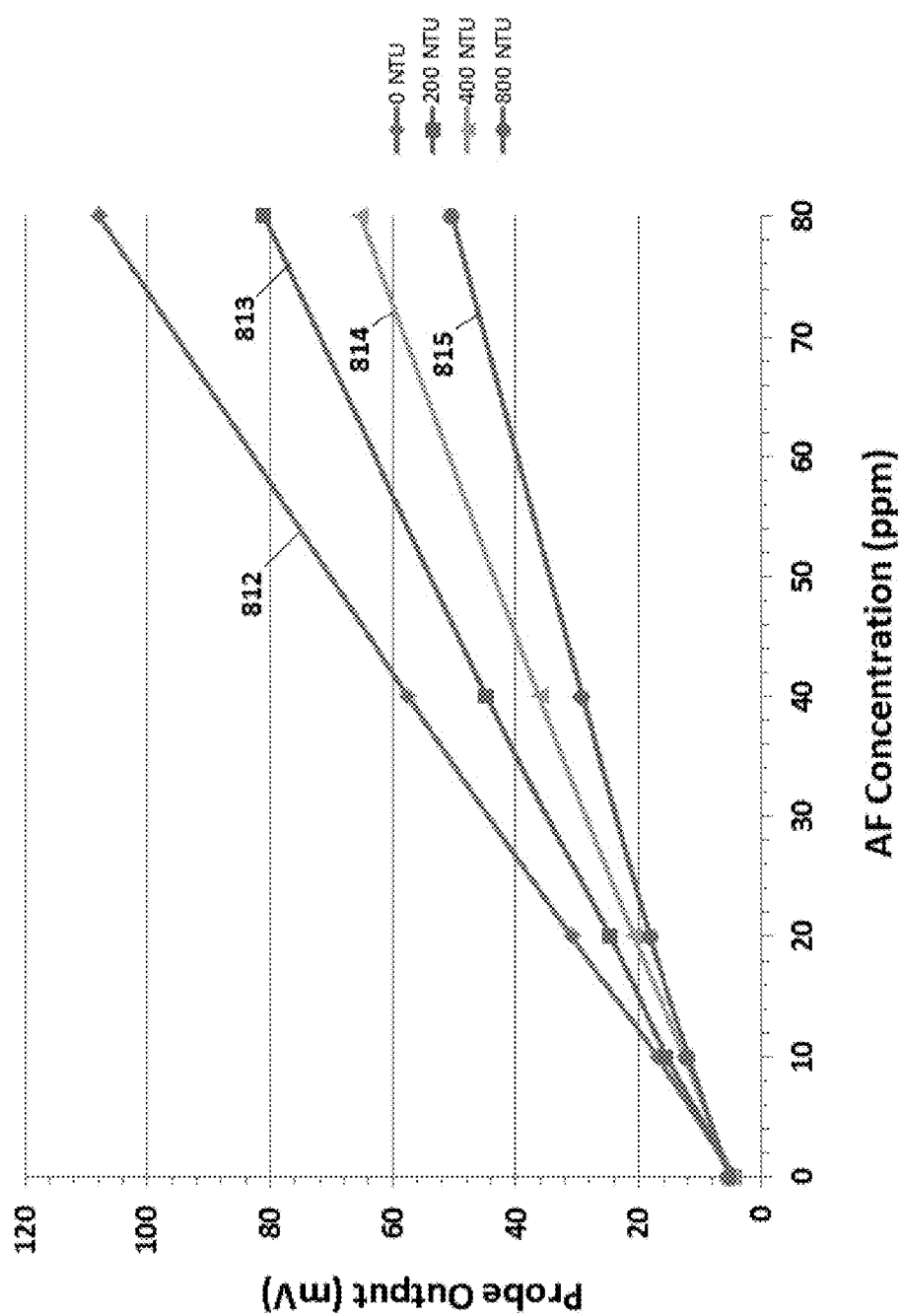

FIG. 8D is a plot of the output of the fluorescence channel of the optical sensor in mV as a function of the AF concentration of the sample in ppm. The fluorescence channel output was a measurement of the intensity of the light fluoresced from the sample, which changed with the AF concentration. The measurement represented in FIG. 8D was performed with samples of varying turbidity, including 0 NTU (812), 200 NTU (813), 400 NTU (814) and 800 NTU (815). It can be seen that, as the turbidity of the sample increased from 0 up to 800 NTU in the example, the fluorescence channel output dropped—almost 54% at an AF concentration of 80 ppm. As a result, using measured turbidity values to correct measured fluorescence values may yield more accurate measurements than if measured fluorescence is used without turbidity correction.

Figure 8E:
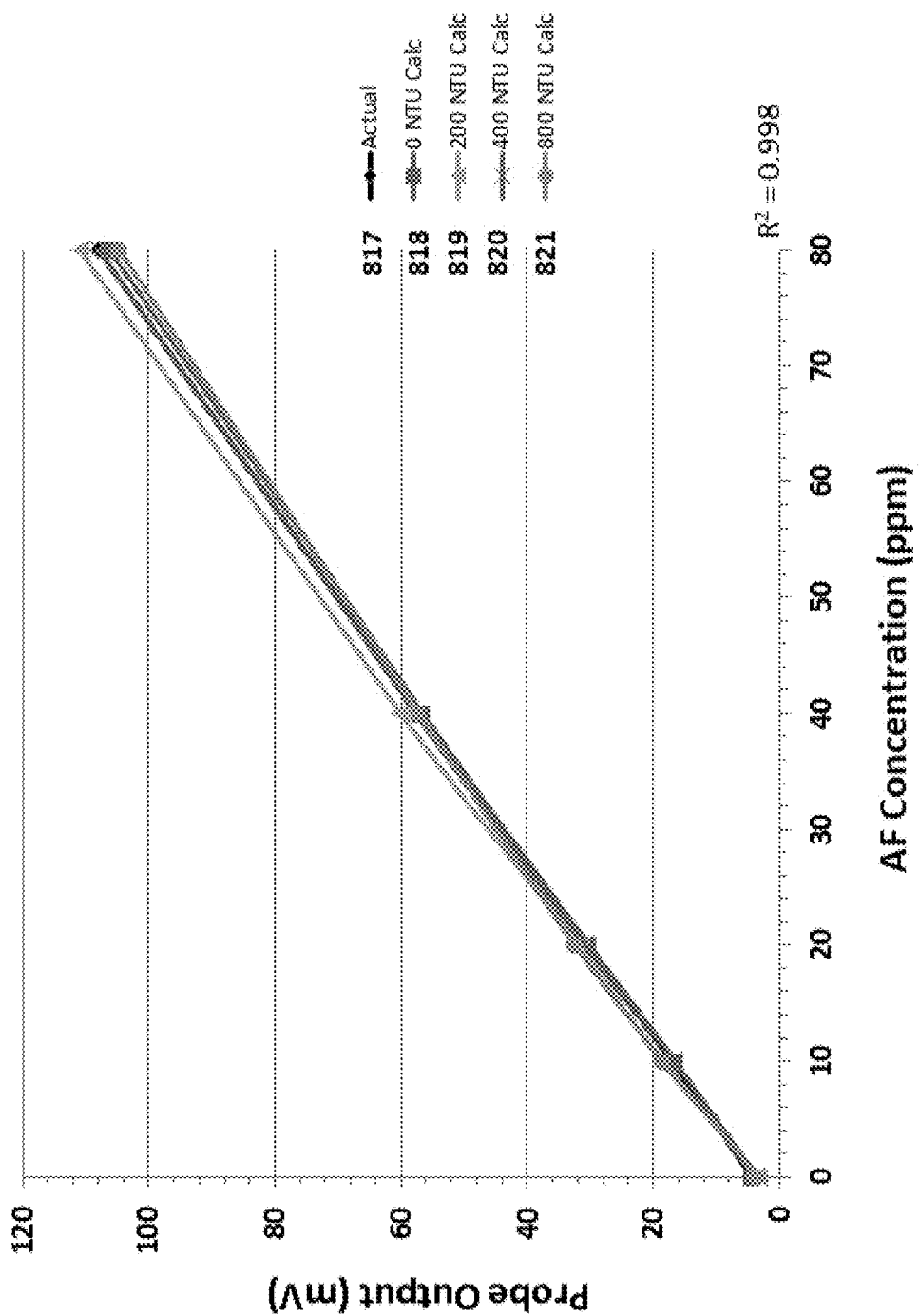

FIG. 8E is a plot of a corrected fluorescence channel output in mV as a function of the AF concentration of the sample in ppm. The output was measured at varying AF concentrations in samples of varying turbidity and mathematically corrected. As with the plot of FIG. 8D, turbidity values of 0 NTU (818), 200 NTU (819), 400 NTU (820) and 800 NTU (821) were used and subsequently compared to the actual fluorescence channel output data (817), resulting in an R-squared value of 0.998. Using corrected fluorescence channel output values, a more consistent relationship between the output and AF concentration was present among samples of varying turbidity, with maximum discrepancy of only about 2.8%. As illustrated in this example, a sensor configured to measure both scattered light and fluoresced light from a sample can utilize both measurements to correlate fluorescence and the fluorophore concentration in the sample regardless of the sample's turbidity.

The invention claimed is:

1. An optical sensor comprising:
   a housing having an optical pathway configured to direct light through an optical window optically connected to the optical pathway into a fluid sample under analysis and receive light from the fluid sample through the optical window;
   a first optical emitter configured to emit light at a first wavelength through the optical pathway and into the fluid sample;
   a second optical emitter configured to emit light at a second wavelength different than the first wavelength through the optical pathway and into the fluid sample;
   an optical detector configured to receive light from the fluid sample through the optical pathway; and
   a controller configured to control the first optical emitter and the second optical to emit light at different times, wherein the optical detector is configured to receive fluorescent emissions through the optical window from the fluid sample in response to light emitted by the first optical emitter, and the optical detector is configured to receive scattered light through the optical window from the fluid sample in response to light emitted by the second optical emitter.

2. The optical sensor of claim 1, wherein the optical pathway defines a major axis extending along the length of the optical pathway and the major axis extends through a center of the optical window and a center of the optical detector.

3. The optical sensor of claim 2, wherein the optical window is an optical lens configured to direct light into the fluid sample from the optical pathway and to receive light from the fluid sample and direct it into the optical pathway.

4. The optical sensor of claim 3, wherein the optical lens consists essentially of a single ball lens.

5. The optical sensor of claim 1, wherein the optical pathway defines a first optical pathway and further comprising a second optical pathway intersecting the first optical pathway at an approximately 90 degree angle, wherein the first optical pathway is positioned between the optical window and the optical detector, and the first optical emitter and the second optical emitter are each positioned to emit light into the second optical pathway.

6. The optical sensor of claim 5, further comprising a partially reflective optical window positioned at an intersection between the first optical pathway and the second optical pathway, wherein the partially reflective optical window is configured to reflect at least a portion of light emitted by the first optical emitter and the second optical emitter from the second optical pathway into the first optical pathway, and the partially reflective optical window is configured to transmit at least a portion of light received from the fluid sample to the optical detector.

7. The optical sensor of claim 6, further comprising a light guide positioned between the partially reflective optical window and the lens.

8. The optical sensor of claim 7, wherein the light guide comprises a quartz rod with polished ends.

9. The optical sensor of claim 6, further comprising a collimating lens positioned between the partially reflective optical window and the optical window.

10. The optical sensor of claim 6, further comprising a beam dump, positioned so that light from the first and second optical emitters transmitted by the partially reflective optical window is incident thereon, and configured to absorb substantially all incident light emitted by the first and second optical emitters.

11. The optical sensor of claim 6, wherein the partially reflective optical window comprises a dichroic filter.

12. The optical sensor of claim 5, wherein the optical detector comprises a first optical detector, and further comprising a second optical detector positioned on an opposite side of the second optical pathway from at least one of the first optical emitter and the second optical emitter.

13. The optical sensor of claim 12, further comprising a third optical pathway intersecting the second optical pathway at an approximately 90 degree angle, wherein the second optical detector is positioned at a terminal end of the third optical pathway opposite at least one of the first optical emitter and the second optical emitter.

14. The optical sensor of claim 13, further comprising a partially reflective optical window positioned at an intersection between the second optical pathway and the third optical pathway, wherein the partially reflective optical window is configured to reflect at least a portion of light emitted by the first optical emitter from the second optical pathway into the third optical pathway, and the partially reflective optical window is configured to transmit at least a portion of light emitted by the second optical emitter into the third optical pathway.

15. The optical sensor of claim 14, wherein the partially reflective optical window comprises a quartz or sapphire window.

16. The optical sensor of claim 15, wherein the partially reflective optical window comprises an anti-reflective coating for an ultraviolet wavelength range.

17. The optical sensor of claim 12, further comprising at least one additional optical pathway intersecting the first optical pathway at an approximately 90 degree angle and disposed between the partially reflective optical window and a terminal end of the first optical pathway opposite the optical window, and wherein the first optical detector comprises a plurality of optical detectors, each configured to detect incident light.

18. The optical sensor of claim 17, further comprising at least one additional partially reflective optical window, each additional partially reflective optical window being positioned at the intersection of the first optical pathway and a corresponding additional optical pathway, and configured to reflect or transmit a select band of light toward at least one corresponding optical detector.

19. The optical sensor of claim 18, further comprising at least one additional filter, disposed between at least one of the additional partially reflective optical windows and at least one of its corresponding optical detectors.

20. The optical sensor of claim 1, further comprising a first optical filter positioned between the first optical emitter and the optical window, and a second optical filter positioned between the optical detector and the optical window, wherein the first optical filter is configured to filter out substantially all wavelengths of light within a range of fluorescent light emitted by the fluid sample, and the second optical filter is configured to filter out substantially all wavelengths of light emitted by the first optical emitter but pass wavelengths from the second optical emitter, fluorescent emissions emitted from the fluid sample in response to the light from the first optical emitter, and light scattered by the fluid sample in response to light from the second optical emitter.

21. The optical sensor of claim 1, wherein the first wavelength ranges from 255 nanometers (nm) to 700 nm, and the second wavelength ranges from 800 nm to 1100 nm.

22. The optical sensor of claim 21, wherein the first wavelength ranges from 265 nm to 290 nm, and the second wavelength ranges from 800 nm to 900 nm.

23. The optical sensor of claim 1, wherein the housing is configured to be inserted into a T-section of pipe with the optical window positioned in the fluid sample flowing through the T-section of pipe.

24. The optical sensor of claim 1, wherein the housing is configured to be inserted into a port of a fluid vessel with the optical window positioned in the fluid sample flowing through the port of the fluid vessel.

25. The optical sensor of claim 1, wherein the housing defines a bottom surface, the optical window extends distally from the bottom surface into the fluid sample, and further comprising a non-optical sensor positioned on the bottom surface adjacent the optical window.

26. The optical sensor of claim 25, wherein the non-optical sensor comprises at least one of a pH sensor, a conductivity sensor, and a temperature sensor.

27. A method comprising:
emitting light at a first wavelength by a first optical emitter through an optical pathway of a housing and an optical window optically connected to the optical pathway into a fluid sample under analysis;
receiving fluorescent emissions emitted by the fluid sample through the optical window and the optical pathway by an optical detector;
emitting light at a second wavelength different than the first wavelength by a second optical emitter through the optical pathway and the optical window and into the fluid sample under analysis, wherein light at the second wavelength is emitted at a different time than light at the first wavelength is emitted; and
receiving light scattered by the fluid sample through the optical window and the optical pathway by the optical detector.

28. The method of claim 27, wherein the optical pathway defines a first optical pathway, and wherein emitting light at a first wavelength and emitting light at a second wavelength through the optical pathway comprises directing the light at the first wavelength and second wavelength into a second optical pathway intersecting the first optical pathway at an approximately 90 degree angle.

29. The method of claim 28, further comprising reflecting at least a portion of light emitted by the first optical emitter and the second optical emitter from the second optical pathway into the first optical pathway by a partially reflective optical window, and transmitting at least a portion of light received from the fluid sample to the optical detector through the partially reflective optical window.

30. The method of claim 28, wherein the optical detector comprises a first optical detector, and further comprising receiving light from at least one of the first and second optical emitters with a second optical detector via a third optical pathway, wherein the third optical pathway intersects the second optical pathway at an approximately 90 degree angle.

31. The method of claim 30, further comprising reflecting at least a portion of light emitted by the first optical emitter from the second optical pathway into the third optical pathway and toward the second optical detector by a partially reflective optical window.

32. The method of claim 27, further comprising passing light emitted by the first optical emitter through a first optical filter to filter out substantially all wavelengths of light within a range of fluorescent light emitted by the fluid sample, and passing light received from the fluid sample through a second optical filter to filter out substantially all wavelengths of light emitted by the first optical emitter and the second optical emitter.

33. The method of claim 27, further comprising determining at least one characteristic of the fluid sample based on the received fluorescent emissions from the sample.

34. The method of claim 33, wherein the at least one characteristic is the fluorophore concentration of the sample.

35. The method of claim 33, wherein the determining of the at least one characteristic comprises adjusting at least one characteristic based on the received scattered light from the sample.

36. The method of claim 27, further comprising determining at least one characteristic of the fluid sample with a non-optical sensor, the non-optical sensor comprising at least one of a pH sensor, a conductivity sensor, and a temperature sensor.

37. A system comprising:
an optical sensor that includes a housing having an optical pathway configured to direct light through an optical window optically connected to the optical pathway into a fluid sample under analysis and receive light from the fluid sample through the optical window, a first optical emitter positioned to direct light through the optical window and the optical pathway into the fluid sample, a second optical emitter positioned to direct light through the optical window and the optical pathway into the fluid sample, and an optical detector positioned to receive light returned from the fluid sample through the optical window and the optical pathway; and
one or more controllers configured to:
control the first optical emitter to emit light at a first wavelength through the optical pathway into the fluid sample under analysis;
detect fluorescent emissions via the optical detector that are emitted by the fluid sample and returned back through the optical pathway;
control the second optical emitter to emit light at a second wavelength different than the first wavelength through the optical pathway and into the fluid sample under analysis; and
detect light scattered by the fluid sample and received through the optical pathway by the optical detector.

38. The system of claim 37, wherein the optical detector comprises a first detector, a second detector, and a selectively reflective optical component, configured so that the selectively reflective optical component directs at least a portion of the light incident from the sample to the first detector and directs at least a portion of light incident from the sample to the second detector.

39. The system of claim 38, wherein the optical detector is configured so that the selectively reflective optical component directs light scattered off of the sample to one of the first and second detectors and fluoresced light from the sample to the other of the first and second detector.

40. The system of claim 37, wherein the one or more controllers controls the first optical emitter and the second optical emitter to emit light in an alternating sequence.

41. The system of claim 37, wherein the one or more controllers determines at least one characteristic of the sample based on the detected fluorescent emissions.

42. The system of claim 41, wherein the one or more controllers adjusts the at least one determined characteristic based on the detected light scattered by the fluid sample.

43. The system of claim 37, wherein the optical pathway defines a first optical pathway and further comprising a second optical pathway intersecting the first optical pathway at an approximately 90 degree angle, wherein the first optical pathway is positioned between the optical window and the optical detector, and the first optical emitter and the second optical emitter are each positioned to direct light into the second optical pathway.

44. The system of claim 43, wherein the optical detector comprises a first optical detector, and further comprising a second optical detector positioned on an opposite side of the second optical pathway from at least one of the first optical emitter and the second optical emitter.

45. They system of claim 43, further comprising:
a third optical pathway intersecting the second optical pathway at an approximately 90 degree angle, wherein the second optical detector is positioned at a terminal end of the third optical pathway opposite at least one of the first optical emitter and the second optical emitter; and a partially reflective optical window positioned at an intersection between the second optical pathway and the third optical pathway, wherein the partially reflective optical window is configured to reflect at least a portion of light emitted by the first optical emitter from the second optical pathway into the third optical pathway, and the partially reflective optical window is configured to transmit at least a portion of light emitted by the second optical emitter into the third optical pathway.

46. The system of claim 37, further comprising a non-optical sensor in communication with the one or more controllers and configured to detect at least one of a temperature, a conductivity, or a pH of the fluid sample.

47. The system of claim 37, wherein the one or more controllers is configured to detect fluorescent emissions emitted by the fluid sample and received through the optical pathway via the optical detector by at least receiving, subsequent to ceasing emission from the first optical emitter, light fluoresced from the fluid sample in response to incident light emitted from the first optical emitter.

48. The system of claim 37, wherein the one or more controllers is configured to detect fluorescent emissions emitted by the fluid sample and received through the optical pathway via the optical detector by at least receiving, while emitting light from the first optical emitter, light fluoresced from the fluid sample in response to incident light emitted from the first optical emitter.

49. The system of claim 37, wherein fluorescent emissions are detected in at least two fluorescent channels, each fluorescent channel corresponding to a particular wavelength or wavelength band of light fluoresced from the sample.

50. The system of claim 49, wherein the optical detector comprises a plurality of detectors, such that light in each fluorescent channel is directed to a corresponding detector.

51. A method comprising:
illuminating a fluid sample through an optical window optically connected to an optical pathway with light of a first wavelength;
collecting fluorescent emissions from the fluid sample through the optical window and the optical pathway;
filtering out substantially all wavelengths of light except wavelengths of the fluorescent emissions and detecting a magnitude of the fluorescent emissions;
subsequent to terminating illumination of the fluid sample with light of the first wavelength, illuminating the fluid sample through the optical window and the optical pathway with light of a second wavelength;
collecting scattered light through the optical window and the optical pathway; and
filtering out substantially all wavelengths of light except wavelengths of the scattered light and detecting a magnitude of the scattered light.

52. The method of claim 51, wherein illuminating the fluid sample with light of the first wavelength comprises emitting light from a first light source toward a partially reflective optical window that splits the light and directs a portion of the light toward the optical window, and illuminating the fluid sample with light of the second wavelength comprises emitting light from a second light source different than the first light source toward the partially reflective optical window that splits the light and directs a portion of the light toward the optical window.

53. The method of claim 52, wherein collecting fluorescent emissions from the fluid sample comprises passing at least a portion of the fluorescent emissions through the partially reflective optical window, and collecting scattered light comprises passing at least a portion of the scattered light through the partially reflective optical window.

54. The method of claim 51, wherein illuminating the fluid sample with the first wavelength and illuminating the fluid sample with the second wavelength comprises alternatingly illuminating the fluid sample with the first and second wavelengths of light.

55. The method of claim 51, wherein detecting the magnitude of the fluorescent emissions comprises determining a concentration of a fluorescing species in the fluid sample, and detecting the magnitude of the scattered light comprises determining a turbidity of the fluid sample.

56. The method of claim 51, wherein filtering out substantially all wavelengths of light except wavelengths of the fluorescent emissions comprises filtering out all wavelengths of light except wavelengths of the fluorescent emissions, and filtering out substantially all wavelengths of light except wavelengths of the scattered light comprises filtering out all wavelengths of light except wavelengths of the scattered light.

57. The method of claim 51, wherein the first wavelength is within an ultraviolet spectrum and the second wavelength is within an infrared spectrum.

58. The method of claim 51, further comprising detecting an electrical conductivity of the fluid sample via a sensor interface adjacent the optical window and detecting a temperature of the fluid sample via a sensor interface adjacent the optical window.

* * * * *